(12) United States Patent
Nottingham

(10) Patent No.: US 9,084,683 B2
(45) Date of Patent: Jul. 21, 2015

(54) SPINAL IMPLANT SYSTEM AND METHOD

(75) Inventor: Paul Nottingham, Alamo, CA (US)

(73) Assignee: PBN Spinal Implants, LLC, Alamo, CA (US)

( * ) Notice: Subject to any disclaimer, the term of this patent is extended or adjusted under 35 U.S.C. 154(b) by 748 days.

(21) Appl. No.: 13/345,154

(22) Filed: Jan. 6, 2012

(65) Prior Publication Data
US 2012/0179260 A1 Jul. 12, 2012

Related U.S. Application Data

(60) Provisional application No. 61/460,811, filed on Jan. 7, 2011.

(51) Int. Cl.
| | | |
|---|---|---|
| *A61F 2/44* | (2006.01) | |
| *A61F 2/46* | (2006.01) | |
| *A61B 17/02* | (2006.01) | |
| *A61F 2/28* | (2006.01) | |
| *A61F 2/30* | (2006.01) | |
| *A61B 17/28* | (2006.01) | |

(52) U.S. Cl.
CPC ............. *A61F 2/4455* (2013.01); *A61B 17/025* (2013.01); *A61F 2/4425* (2013.01); *A61F 2/4611* (2013.01); *A61B 17/2804* (2013.01); *A61F 2/4684* (2013.01); *A61F 2002/2817* (2013.01); *A61F 2002/2835* (2013.01); *A61F 2002/304* (2013.01); *A61F 2002/30364* (2013.01); *A61F 2002/30401* (2013.01); *A61F 2002/30451* (2013.01); *A61F 2002/30553* (2013.01); *A61F 2002/30607* (2013.01); *A61F 2002/30614* (2013.01); *A61F 2002/30616* (2013.01); *A61F 2002/448* (2013.01); *A61F 2002/4475* (2013.01); *A61F 2002/4485* (2013.01); *A61F 2310/00017* (2013.01); *A61F 2310/00023* (2013.01); *A61F 2310/00179* (2013.01)

(58) Field of Classification Search
USPC .......................................... 606/99; 623/17.16
See application file for complete search history.

(56) References Cited

U.S. PATENT DOCUMENTS

| | | | |
|---|---|---|---|
| 4,997,432 A | 3/1991 | Keller | |
| 5,961,554 A * | 10/1999 | Janson et al. | ............... 623/17.16 |
| 6,146,421 A | 11/2000 | Gordon et al. | |
| 6,562,074 B2 | 5/2003 | Gerbec et al. | |
| 6,726,720 B2 | 4/2004 | Ross et al. | |
| 6,936,071 B1 | 8/2005 | Marnay et al. | |
| 7,235,101 B2 | 6/2007 | Berry et al. | |
| 7,488,330 B2 | 2/2009 | Stad | |

(Continued)

OTHER PUBLICATIONS http://www.alphatecspine.com/products/mis/glif.asp, "Alphatec Spine Guyer Lumbar Interbody Fusion (GLIF)", accessed Nov. 12, 2011.

*Primary Examiner* — Christian Sevilla
(74) *Attorney, Agent, or Firm* — Woodard, Emhardt, Moriarty, McNett & Henry LLP

(57) ABSTRACT

A spinal implant system is disclosed. The system disclosed has a first footing adapted for inter-vertebral contact with a first vertebral body, a second footing adapted for inter-vertebral contact with a second vertebral body adjacent to the first vertebral body; and, a support slideably insertable between said first footing and said second footing while said first and second footings are in-situ between said first and second vertebral bodies. The footings provide a path for the support. Distractor instruments are disclosed. Methods of use, in surgery, are also disclosed.

23 Claims, 55 Drawing Sheets

(56) References Cited

U.S. PATENT DOCUMENTS

| | | |
|---|---|---|
| 7,674,294 B2 | 3/2010 | Karahalios et al. |
| 7,695,516 B2 | 4/2010 | Zeegers |
| 7,708,776 B1 | 5/2010 | Blain et al. |
| 7,753,956 B2 | 7/2010 | de Villiers et al. |
| 7,758,646 B2 | 7/2010 | Khandkar et al. |
| 7,780,731 B2 | 8/2010 | Marnay et al. |
| 7,811,325 B2 | 10/2010 | Cannon et al. |
| 7,867,279 B2 | 1/2011 | Hester et al. |
| 2004/0143332 A1 | 7/2004 | Krueger et al. |
| 2005/0267581 A1 | 12/2005 | Marnay et al. |
| 2006/0129244 A1* | 6/2006 | Ensign ............. 623/17.16 |
| 2007/0260316 A1 | 11/2007 | Schneid et al. |
| 2008/0058940 A1 | 3/2008 | Wu et al. |
| 2008/0140204 A1 | 6/2008 | Heinz |
| 2009/0076616 A1 | 3/2009 | Duggal et al. |
| 2009/0088850 A1 | 4/2009 | Froehlich |
| 2009/0132051 A1 | 5/2009 | Moskowitz et al. |
| 2010/0070036 A1 | 3/2010 | Implicito |
| 2010/0082110 A1 | 4/2010 | Belliard |
| 2010/0125334 A1 | 5/2010 | Krueger |
| 2010/0286784 A1 | 11/2010 | Curran et al. |
| 2011/0184522 A1 | 7/2011 | Melkent et al. |

* cited by examiner

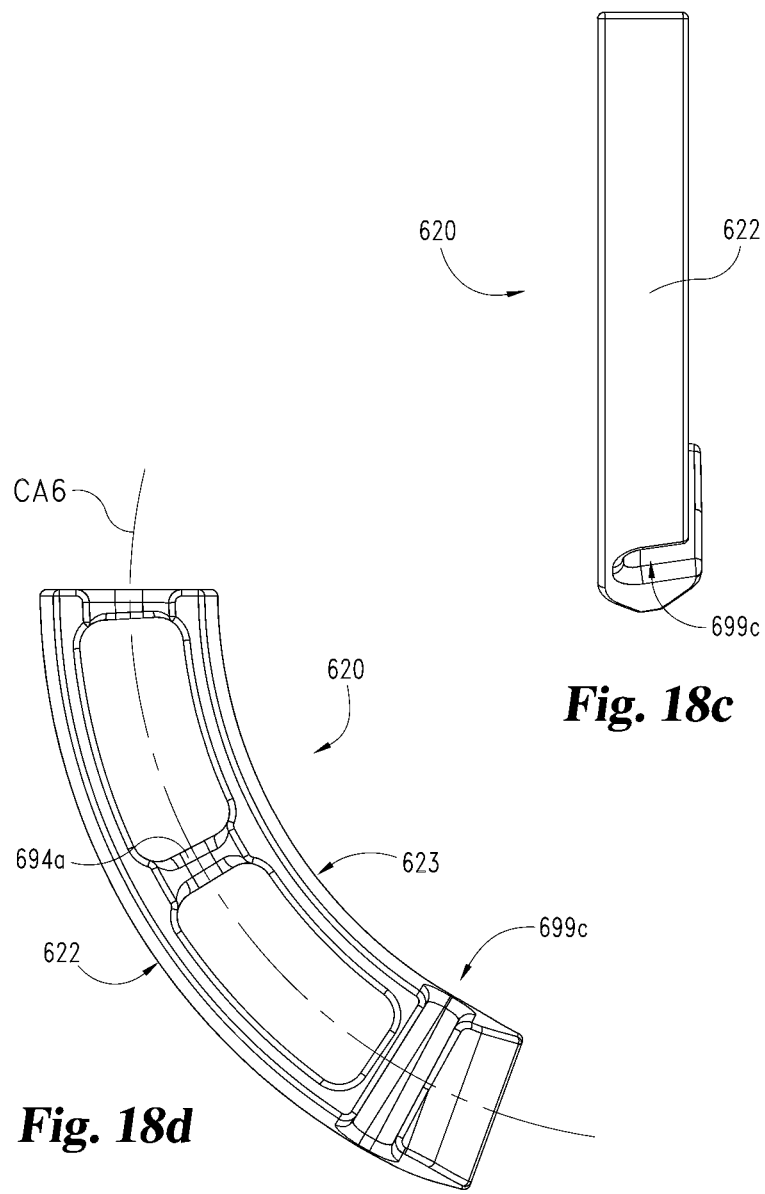

US 9,084,683 B2

SPINAL IMPLANT SYSTEM AND METHOD

CROSS-REFERENCE TO RELATED APPLICATION

This application claims the benefit of U.S. Provisional Application No. 61/460,811 filed Jan. 7, 2011, entitled MODULAR INTERBODY CAGE AND VERTEBRA DISTRACTOR, which is hereby incorporated by reference.

BACKGROUND

The present invention relates to a modular interbody cage and/or other spinal implant and vertebra distractor, as well as surgical methods of use.

Spinal fusion is a procedure often indicated when the spine has been injured or experienced degeneration, or where excessive pain is being experienced due to damage or injury to structures within an intervertebral space between adjacent vertebra. Such spinal fusion can take place in a variety of different ways, and is often accomplished along with placement of rods in a posterior approach surgical procedure to secure adjacent vertebras together. Often, when the adjacent vertebras are fused together, some form of cage is placed within a disc or intervertebral body space. Disc material is removed from the interbody space. A cage packed with bone growth material is then placed within the space. The adjacent vertebra fuse together through the interbody space and through the cage (or cages) which distract and stabilize the vertebra while fusion occurs.

Interbody cages and other implants come in a variety of different configurations and can be implanted anteriorly through a trans-abdominal approach, or posteriorly (or posteriorly laterally). Generally, posterior approaches are desirable in that the procedure can avoid the complications associated with major abdominal surgery.

SUMMARY

The claims, and only the claims, define the invention. Merely by way of partial example, in certain aspects, the present invention provides unique spinal implant systems that can effectively deliver an implant to fuse adjacent vertebra in a spine. In accordance with some forms of the invention, such spinal implant systems are configured to deliver the implant along a path. In some embodiments, a spinal implant system is provided which comprises a first footing adapted for inter-vertebral contact with a first vertebral body, a second footing adapted for inter-vertebral contact with a second vertebral body, and a support slideably insertable between the first and second footings. The first and second footings provide a path wherein the support is inserted by being advanced in a curvilinear or generally perpendicular path along the curvilinear path created by the first and second footings.

Further forms, objects, features, aspects, benefits, advantages, and embodiments of the present invention will become apparent from a detailed description and drawings provided herewith.

BRIEF DESCRIPTION OF THE DRAWINGS

FIG. 4b is a front, elevation view of an alternative implant to FIG. 4a.
FIGS. 18a-18e are views of an implant footing of FIG. 17a shown in isolation, with 18a and 18b being perspective views, 18c a side elevation, 18d a plan view, and 18e a rear elevation.

BRIEF DESCRIPTION OF THE PREFERRED EMBODIMENTS

Figure 1:
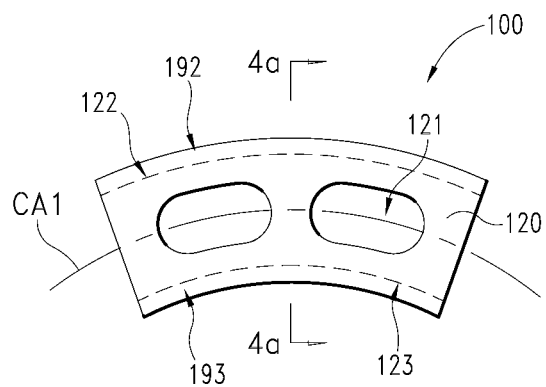
FIG. 1 is a plan view of an implant.
Figure 2:
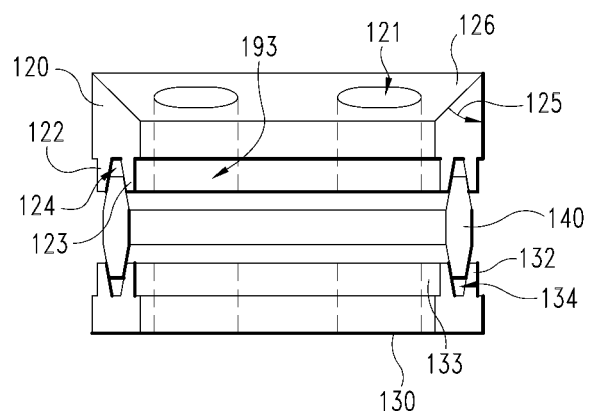
FIG. 2 is an elevation view of a FIG. 1, showing a lordotic footing-support-footing assembly.
Figure 3:
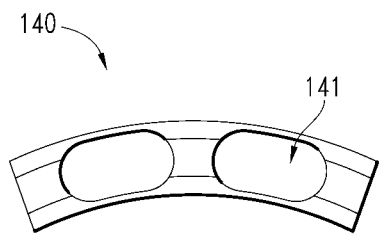
FIG. 3 is a plan view of a middle support.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

FIGS. 1-23g show mere examples of that which is claimed. Those examples are described here. As used in the claims and the specification, the following terms have the following defined meanings:

The term "adjacent" means being located relatively next to or near another object. or close in spacial location.

The terms "advanced" and "advance-able" mean, respectively, having been or being capable of being moved in location relative to some reference. That includes but is not limited to a movement along a path or a movement in or along a particular direction. This may include a path or predefined track. Examples of advance-able systems include but are not limited to systems that utilize a pushing member, a cord or other tension member, a worm gear, a rack and gear, fluid pressure, or other mechanism to apply a force or to allow a force to be applied to an object permitting it to move in location relative to some reference.

The term "bone growth material" means a substance with characteristics that promote or provide for the formation, growth, in-growth, and/or regrowth of bone. Bone growth material includes but is not limited to man-made materials such as synthetics, polymers, metals and ceramics, biologic materials including plants, plant extracts, bone, bone chips, bone shavings, proteins, activators, and otherwise (whether from human, bovine, porcine or other animal origins), and/or naturally occurring materials including minerals, as well as blends, coatings, and/or other combinations of the foregoing. Bone growth material may be solid, liquid, paste, gel or other non-gaseous state.

The term "cage" means a physical structure or assembly that is structurally strong enough to provide inter-vertebral support and which has at least one void and at least one opening exposing the void to the outside of the cage.

The term "central" means generally in the center of or at least encompassing the centroid of a shape, volume, area, structure, assembly or other object or shape.

The term "void" means a volume that is either substantially absent of material and/or which is adapted to be filled with, or at least receive, some other material, such as for example bone growth material.

The term "corresponding" means having a structural and/or functional relationship or associaton between at least two elements.

The term "curvilinear path" means a path that includes at least one curve to change direction. It includes, but is not limited to, paths which are fully curved as well as paths which also include one or more linear segments. It includes curves with are constant radius (arcs of circle(s)) as well as non-constant radii of curvature. It includes paths which curve in one general direction (left, right, up, down), as well as paths which are serpentine. It includes paths which are coplaner and/or which are three dimensional.

The term "distal" means away from the operator during use (typically a surgeon), relative to its opposite: proximal.

The term "distract" means to move away from and/or to move apart.

The term "distracting force" means physical opposing forces imparted to distract.

The term "distraction instrument" means the implement including but not limited to a tool or device used to apply a distracting force. In use, it preferably is surgically sterile.

The term "exposing" means presenting or facing an object or surface without a covering to something else.

The term "footing" means a base or supporting structure that contacts (directly and/or indirectly via an intermediary layer or coating) vertebral body bone. A footing may be made primarily of any solid material including but not limited to metal (stainless steel, titanium, alloy(s), or otherwise), bone, ceramic, polymer, and/or a blending or combination thereof. A footing may comprise a foundation and/or a ceiling (e.g. a header). It may be one piece or multi-piece.

The term "generally perpendicular" means a direction or path or portion thereof (straight and/or curvilinear) relative to another direction (such as for example along an axis), namely which is a least between plus or minus 45 degrees to perpendicular to that direction, and (optionally) more preferably between plus or minus 30 degrees to perpendicular to that direction. By contrast, being purely perpendicular means at a 90 degree angle.

The term "height" means the distance as measured from one side of an object to another, typically from the bottom to the top. In context here, such as for an in situ implant, height is along the orientation from person's feet to the person's head.

The term "impart" means to apply (directly or indirectly) or transmit force to an object.

The term "insertable" means physically capable (size and shape) of being inserted, put into place, or introduced into something or in between objects.

The term "interlocked" means united, joined closely, or connected together such that one part limits or constrains motion of another part in at least one, and preferably two or more, direction((s).

The term "inter-vertebral contact" means touching or meeting (directly and/or indirectly via an intermediary layer or coating) vertebral body bone that faces an adjacent vertebral body.

The term "length" means the distance, direction and/or orientation that is perpendicular to an object's height and length. The length may be curvilinear, straight, or otherwise.

The term "loaded" means having a component (such as a footing) mounted on the distal end of a surgical instrument prior to insertion into the surgical site.

The term "longer" along said curvilinear path means extending a greater distance as measured along the curvilinear path than a comparative distance. For example, a footing being longer along said curvilinear path than 15 mm means that the distance along the curvilinear path on which the footing lies is more than 15 mm.

The term "longitudinal axis" means an axis or direction that lies generally along the length of a element an through its central region. It may be linear or in the case of a curved element, curvalinear.

The term "major axis" means a central longitudinal axis that lies substantially along the length of the distractor tool from its proximal end and within the tool's plane of movement.

The term "nested" means located entirely or at least partially within an area or space defined by another. If one object is "nested" within a second object, the first object may be entirely within an area and/or space defined by the second object, or only a portion of the first object may be within the area or space (partially nested). An object that is nested may or may not have a structure or shape that corresponds with the structure or shape of the other object.

The term "proximal" means toward the operator during use (typically a surgeon), relative to its opposite: distal.

The term "transverse footprint" of a part, footing, support and/or implant means the surface area along the transverse plane of a verbral body taken by projecting the total perimeter profile thereof onto a transverse plane (such as by projecting said profile onto the vertebral body).

The term "opening" means a portion of a surface either substantially absent of material and/or which is adapted to be filled with, or at least receive, some other material, such as for example bone growth material. Examples of openings include but are not limited to gaps, holes, apertures, wells, divots, and/or channels.

The term "opposed" means acting and/or positioned in a substantially counter or oppositeorientation, including but not limited to a force that acts in the opposite direction.

The term "loaded" means having an object or objects mounted or placed in position in or on another object and/or path.

The term "offset" means one object lying in a different plane or along a different axis with respect to another object. Offset may include but is not limited to parallel objects. An example of something being offset is two parallel planes that have a space between them.

The term "prong" means a projection extending from a surface or object and with at least one generally free end. A prong may be straight, curved, and/or otherwise. Prongs, if more than one, may or may not be parallel to one another. Prongs also may or may not extend substantially in the same direction as one another.

The term "provide" means making available, supplying, equipping, and/or using.

The term "rigid body" means a structure that does not easily yield or that is not substantially pliant or flexible. The term includes but is not limited to stiff or hard structures. Rigid bodies may or may not be made of ceramic, bone, and/or a metal (such as stainless steel, titanium and/or otherwise).

The term "separation edge" means an edge near the distal end of an instrument where the support leaves the distractor instrument. This normally occurs with the support being within the footings during and/or after it leaves the distractor instrument.

The term "slide interface" means a surface, point and or edge where another surface, point and/or edge meets to form contact (direct or indirect) and/or a path for relative movement therebetween. The surfaces may or may not come into physical contact. The surfaces may be substantailly flat and/or may be contoured such that one surface may slideably move in relation to the other surface. Examples of a slide interface include but are not limited to a smooth surface, a linear rail, and a channel, The term "slideably" means capable of changing position by moving along a path.

The term "spinal implant system" means a medical or vetranarian part, implant and/or an assembly or combination of one or more members to attach to the spine and/or vertebrae.

The term "stop" means a generally rigid member that is in or at the end of a path or track to prevent movement of another object beyond it.

The term "support" means a solid object that is stong enough (alone or at least in combination with another support) to withstand inter-vertebral compressive forces. Supports may be in a variety of shapes and sizes. Supports may or may not be of the fixed, roller, pinned, or simple type. Furthermore, supports may or may not be configured to receive one or more forces along a single direction or two or more forces along a plurality of directions.

The term "track" means a structure or portion of a structure configured to receive and guide an object along a path, route, or course. The term includes but is not limited to channels, rails and guides. A track may be male, female and/or both. A track may or may not be defined by one or more surfaces on other objects.

The term "vertebral body" means the large, portion of a vetebra that is anterior to the pedicles.

The term "width" means the distance, direction and/or orientation as from one side of an object to another that is perpendicular to the objects height and length.

The term "zig-zag" means generally first deviating (zig) from a direction, such as from the major axis, (for example, deviating left) and then deviating (zag) a second generally opposite direction (for example, deviating right). It may include a zig-zag-zig, a zig-zag-zig-zag, or more. Preferrably, but optionally, the second generally opposite direction crosses the major axis. Zig and/or zag may include curved, straight and/or other segments. Zig and/or zag may be coplaner or non-coplaner.

Articles and phases such as, "the", "a", "an", "at least one", and "a first", are not limited to mean only one, but rather are inclusive and open ended to also include, optionally, multiple such elements. Likewise, "comprising" is open ended and inclusive.

The term "and/or" means, inclusively, both "and" (conjunctive) as well as "or" (disjunctively).

With reference to the drawing FIGS. 1-23g, various examples are shown. For simplicity, systems are prefixed in the hundred's digit (e.g. systems and/or implants 100, 200, 300, 400, 500, 600). The ten's digit generally corresponds as follows: 20's for footing, 30's for footing, 40's for support, 60's and 70's for instrumentation, and 80's and 90's for other features. These features in the examples may be hybridized, combined and/or mixed and matched.

Thus, various options include a spinal implant system 100, 200, 300, 400, 500, 600, comprising a first footing 120, 220, 320, 420, 520, 620 adapted for inter-vertebral contact with a first vertebral body VB (see for example FIGS. 5a, 11a, 23a-g). A second footing 130, 230, 330, 430, 530, 630 is adapted for inter-vertebral contact with a second vertebral body adjacent to the first vertebral body. A support 140, 240, 340, 440, 540, 640 is slideably insertable between the first footing and the second footing.

Note, the components, such as footing 530 and/or footing 630, or otherwise, may be single or multiple part. In the example of footings 530 and 630, a second part, cross bar 530a and 630a is optionally attached (by fasteners, welding or otherwise). Compare, FIGS. 20a-20e showing footing 630 without the cross bar.

Figure 4A:
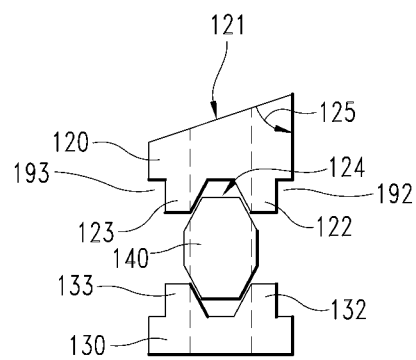
FIG. 4a is a front, elevation view of a FIG. 1 lordotic footing-support-footing assembly.
Figure 4B:
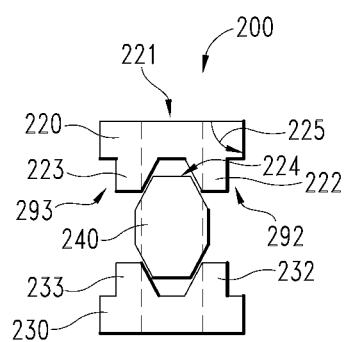
Figure 13A:
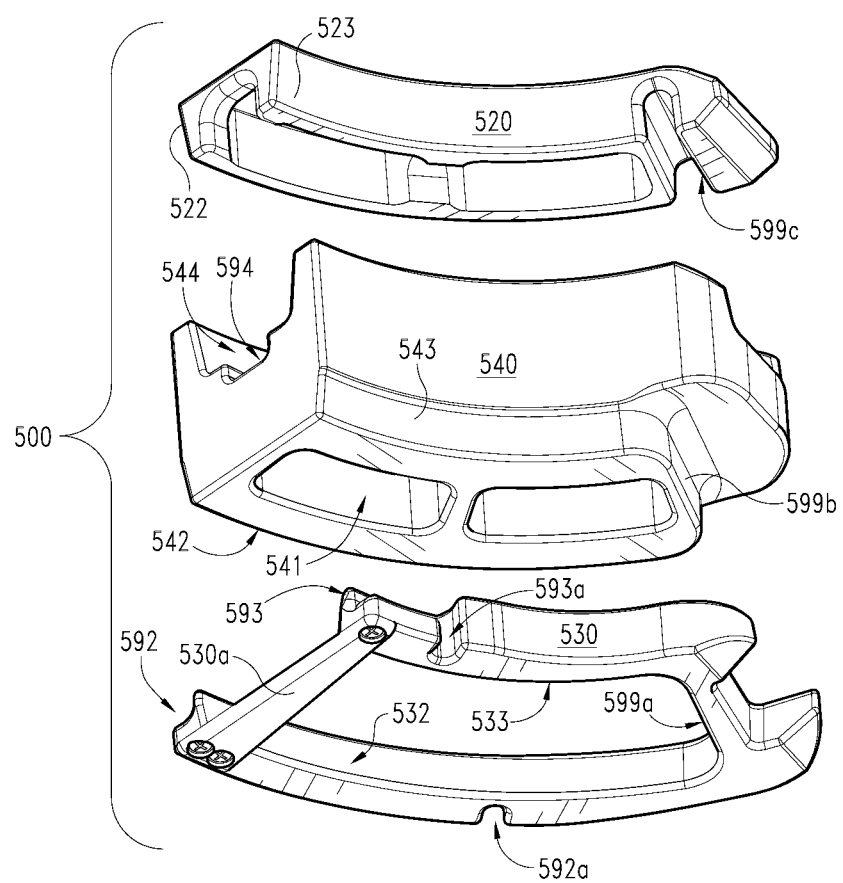
FIGS. 13a-13e are views of an alternative implant, with 13a being an exploded view, 13b and 13d being plan views, 13c a rear view, and 13e a perspective view.

Optionally, the footings may provide a curvilinear path as illustrates with footings 120, 130 in FIGS. 1-3 and 4a, footings 220 and 230 in FIG. 4b, footings 520 and 530 in FIGS. 13a-13-e, and footings 620 and 630 in FIGS. 17a-17e. One or more support is/are adapted to be insertable by being advanced in a curvilinear path along said curvilinear path of said footings while said first and second footings are in-situ between said first and second vertebral bodies.

Figure 7:
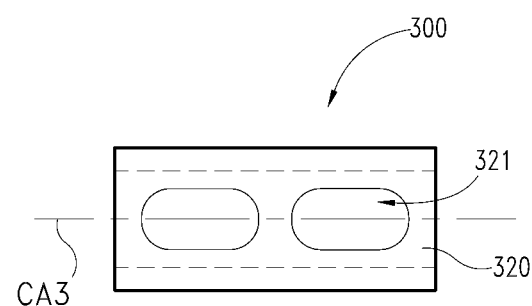
FIGS. 7-9 are an alternative implant.
Figure 8:
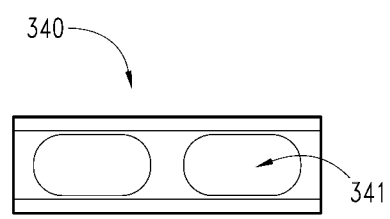
Figure 9:
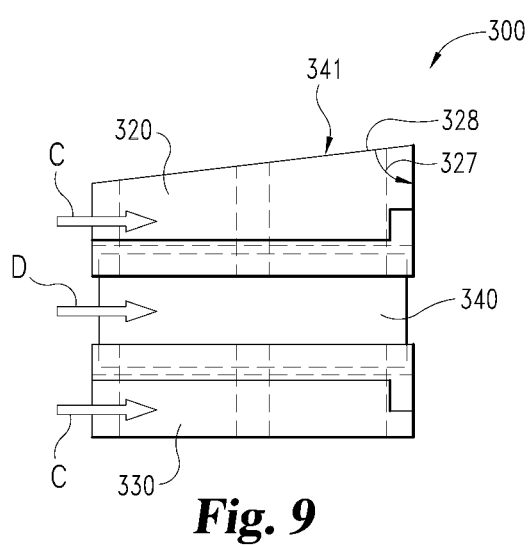
Figure 10:
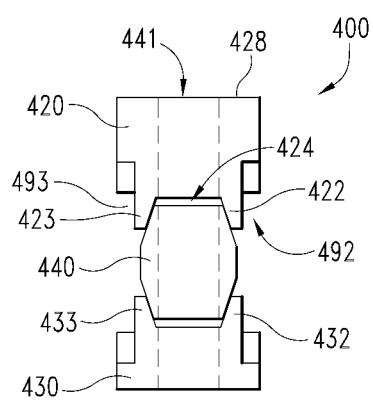
FIG. 10 is an alternative implant.
Figure 11A:
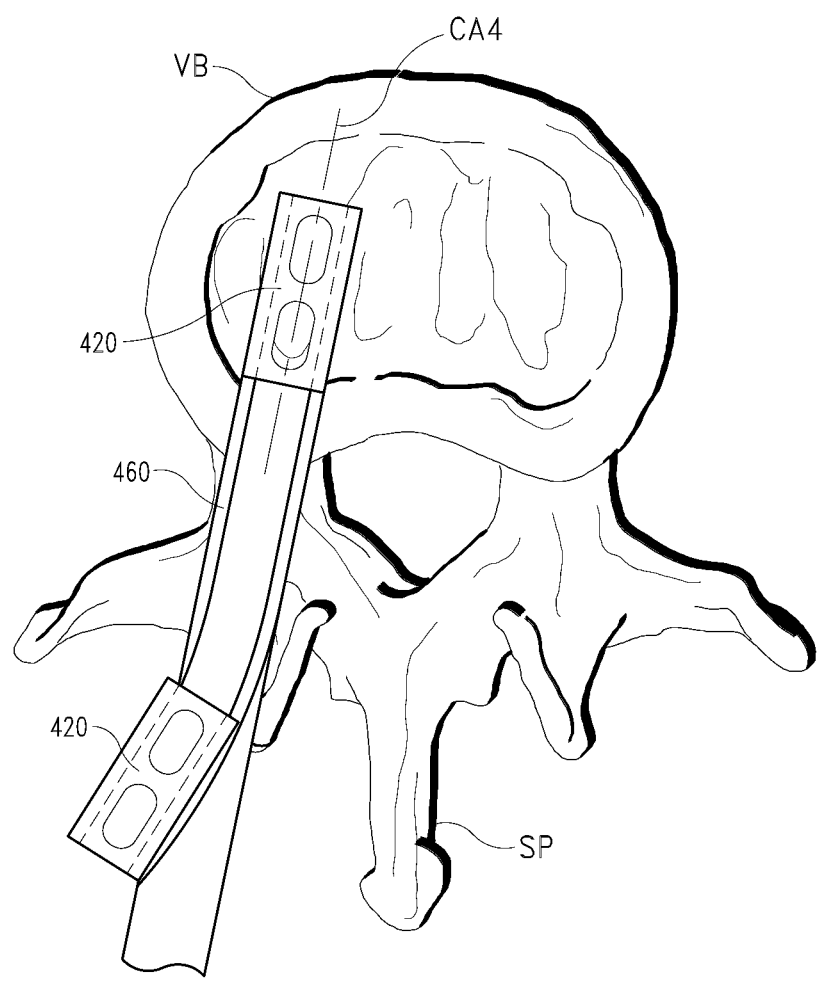
FIGS. 11a and 11b are plan views, in sequence, of the implantation of a linear modular support system through the pedicle.
Figure 11B:
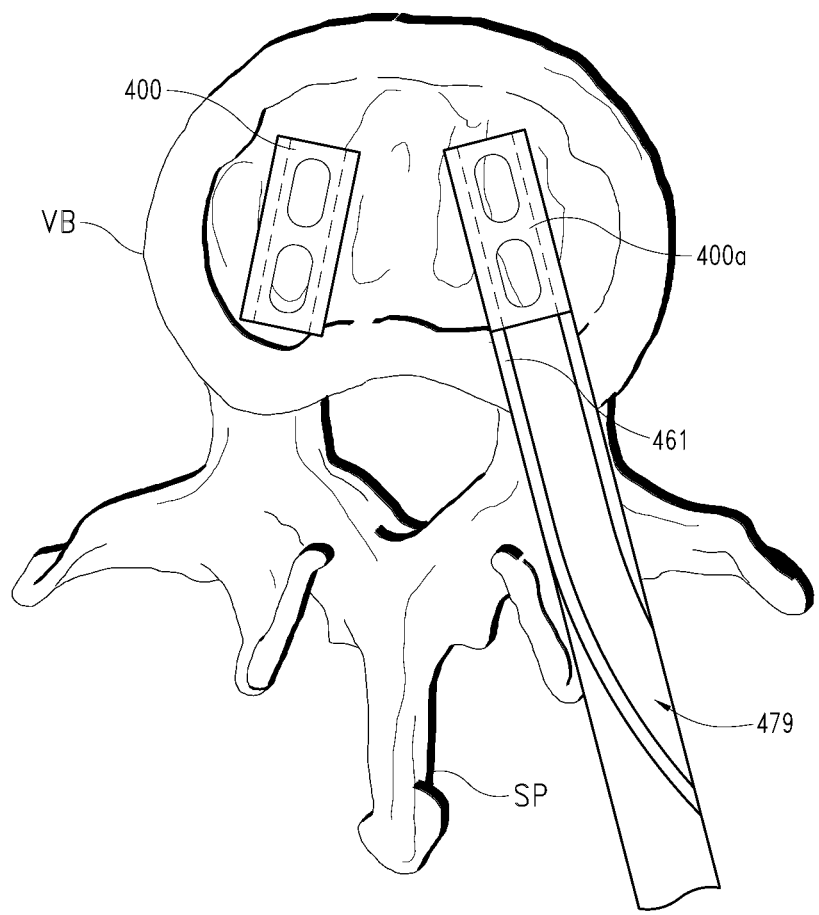
Figure 12:
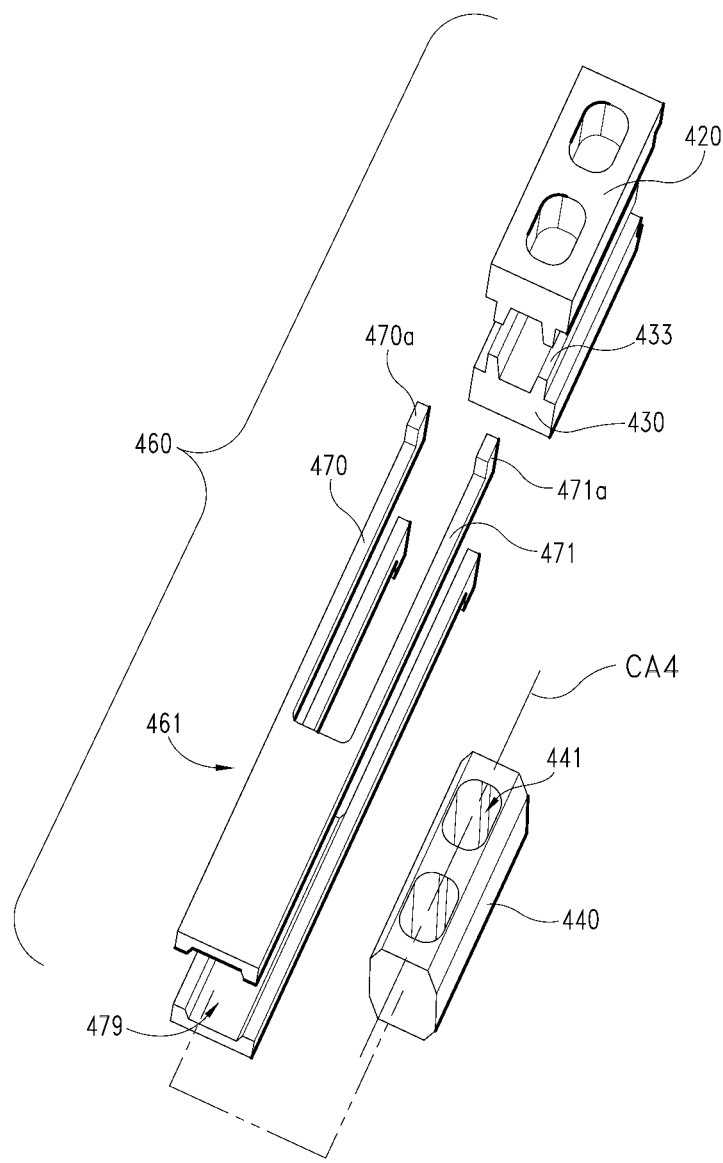
FIG. 12 is a perspective view of a distraction instrument and implant system.

Optionally, they may be otherwise such as providing a straight path as illustrated with footings 320 and 330 in FIGS. 7-9 and footings 420 and 430 in FIG. 10. Also, optionally, the implants and instruments for example of FIGS. 17a-23g could be modified to be straight or linear, rather than the curvilear, arc of a circle arrangement as illustrated. Optional methods of use of such a staight system also include lateral, anterolateral, and/or trans-pedicle approaches to the vertebral body.

Figure 17A:
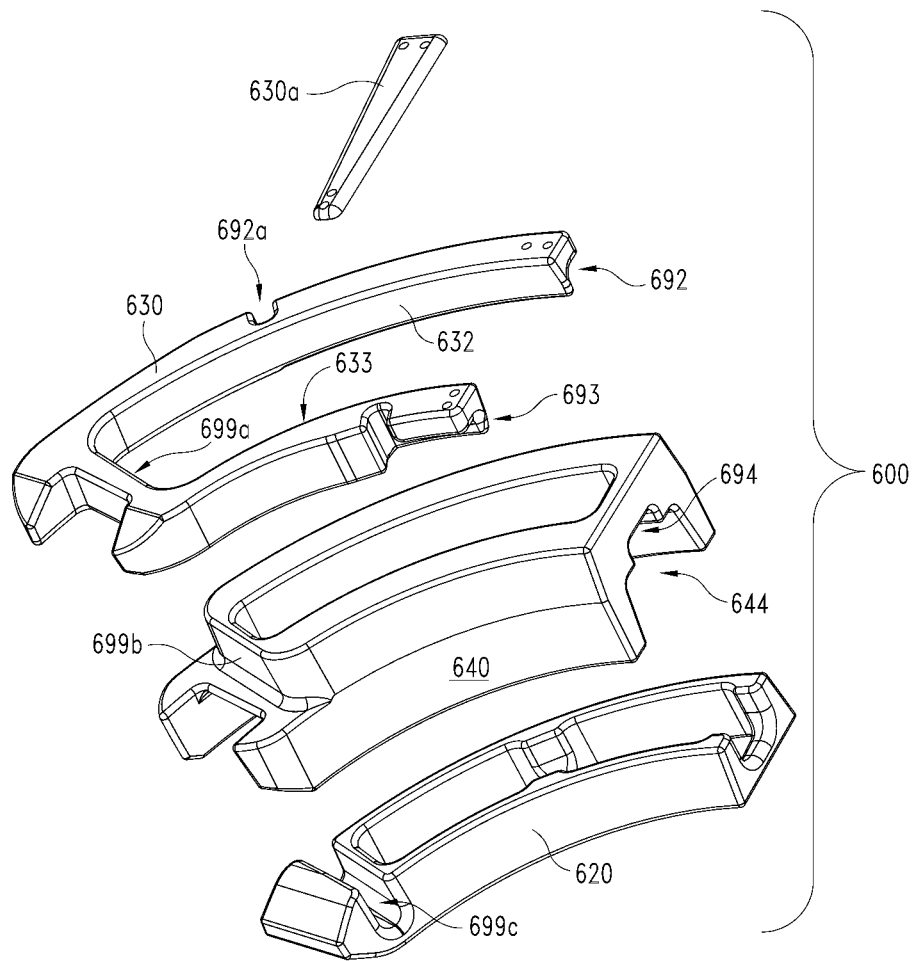
FIGS. 17a-17e are views of an alternative implant, with 17a being an exploded view, 17b, 17c and 17d being perspective views, and 17e a rear view.
Figure 17B:
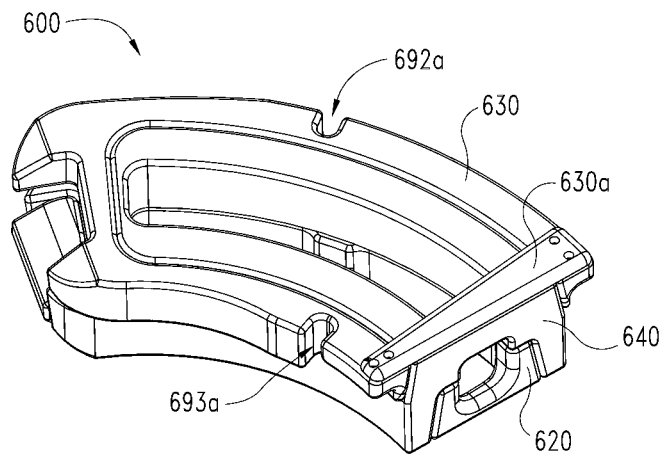
Figure 17C:
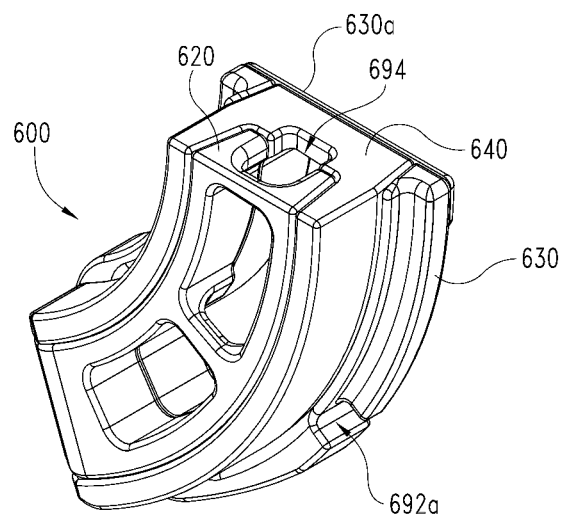
Figure 17D:
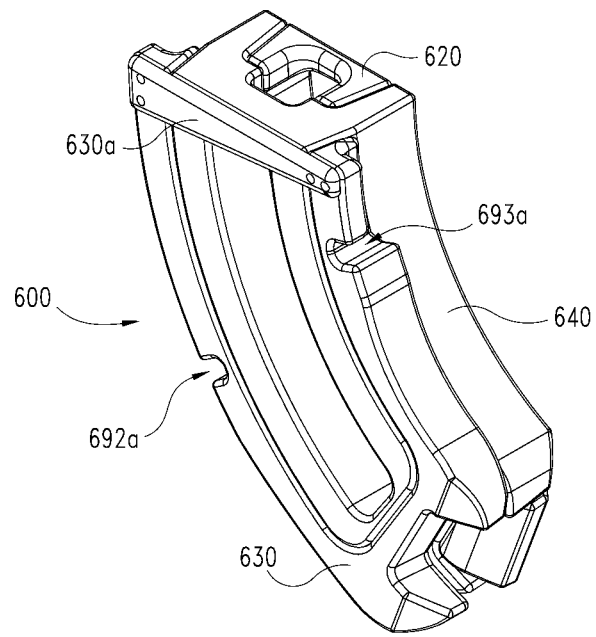
Figure 17E:
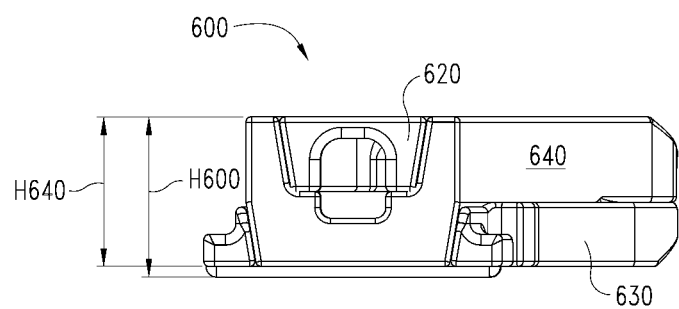

The spinal system may optionally be such that the first footing, the second footing and the support are interlocked to form a rigid body, such as implant 500 in 13e or implant 600 in FIG. 17c, among others shown.

The first footing and the second footing optionally are longer along their path (curvilinear, straight) than their respective width, such as illustrated in FIGS. 13b and 13d, and FIGS. 1, 3, 18d and 19d, among others.

Optionally, the first footing and the second footing each have a transverse footprint, such as illustrated by the area of the full outer shape shown in FIGS. 1, 7, 13b, 18d, 20d, which is smaller than 800 square millimeters. However, such transverse footprint may be a variety of sizes, greater or smaller, and most commonly is less than about 500 square millimeters. The lengths of the footings may vary, but typically are about 25 to 50 millimeters long (straight or curved), and more preferably about 30-40 millimeters long. The widest footing tends to be narrower that the length, although that is optional. When the footings, paths and/or supports are curvilinear (such as arcs of circles), they preferrablly have a radius of curvature between about 20 and 50 millimeters, and more preferably between about 25 and 40 millimeters; and the arc may be any amounts, but preferably is less than 90 degrees, and in some cases is about 70 degrees. All of these dimensions may be varied, and particularly so to accommodate various sized physiology of a patient.

Figure 5A:
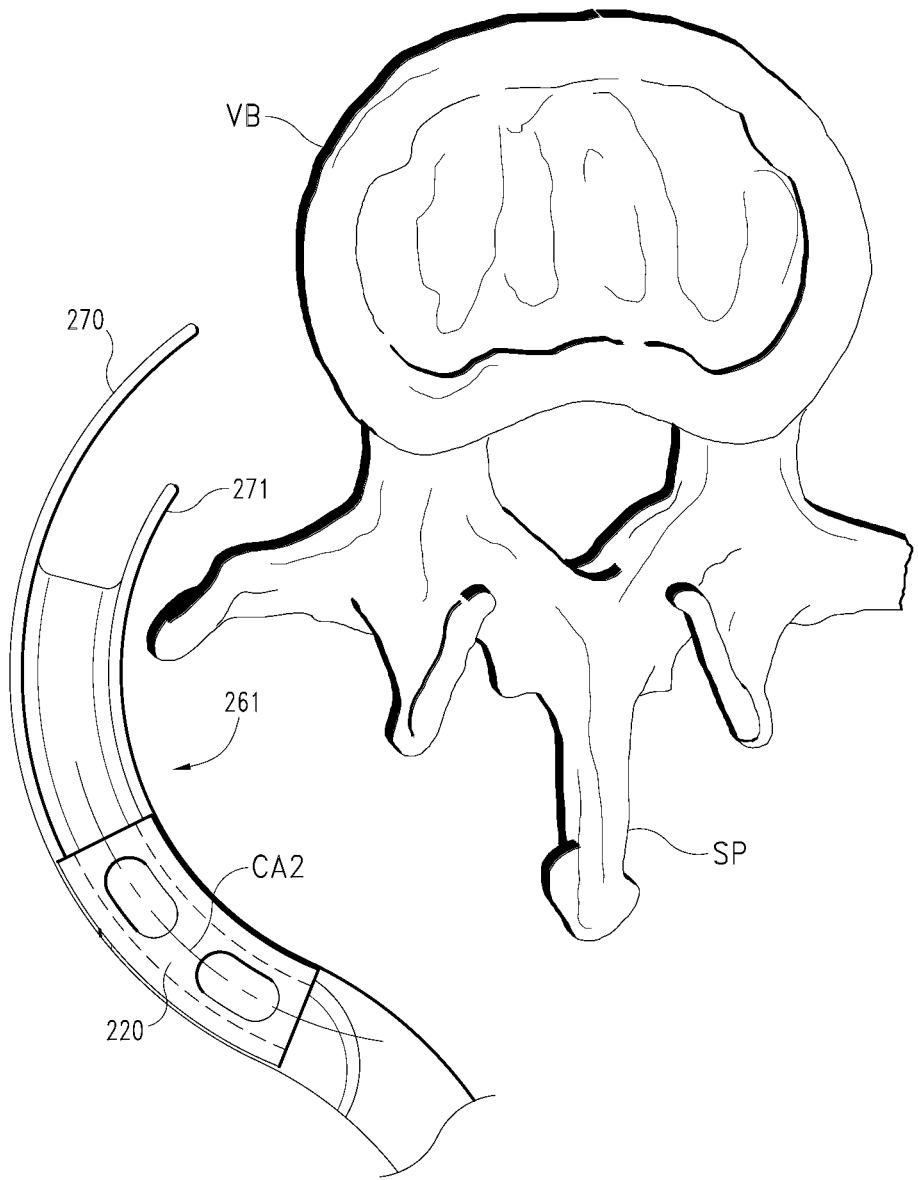
FIGS. 5a-5f are plan views, in sequence, of and example of the implantation of a curvilinear modular support system.
Figure 5B:
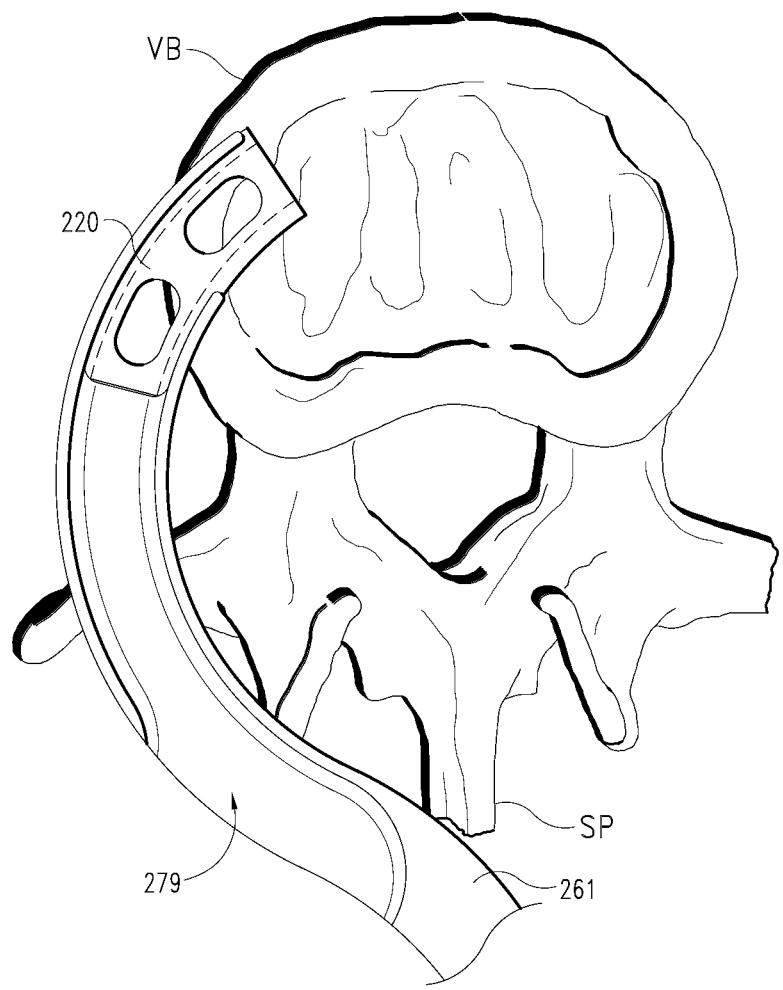
Figure 5C:
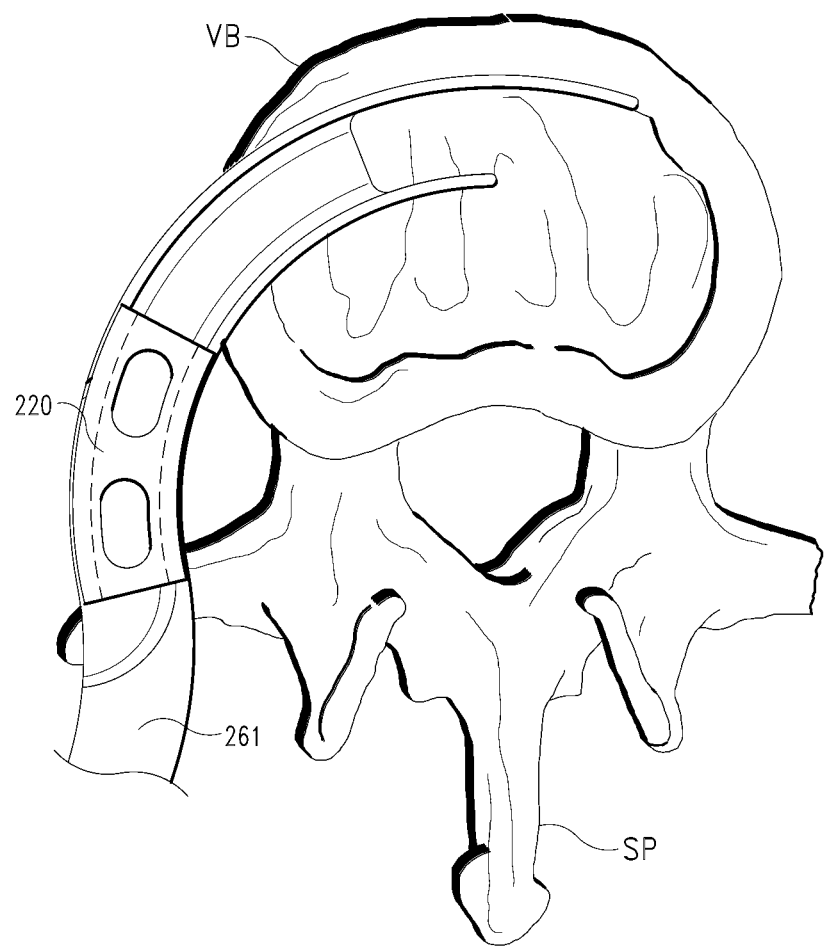
Figure 5D:
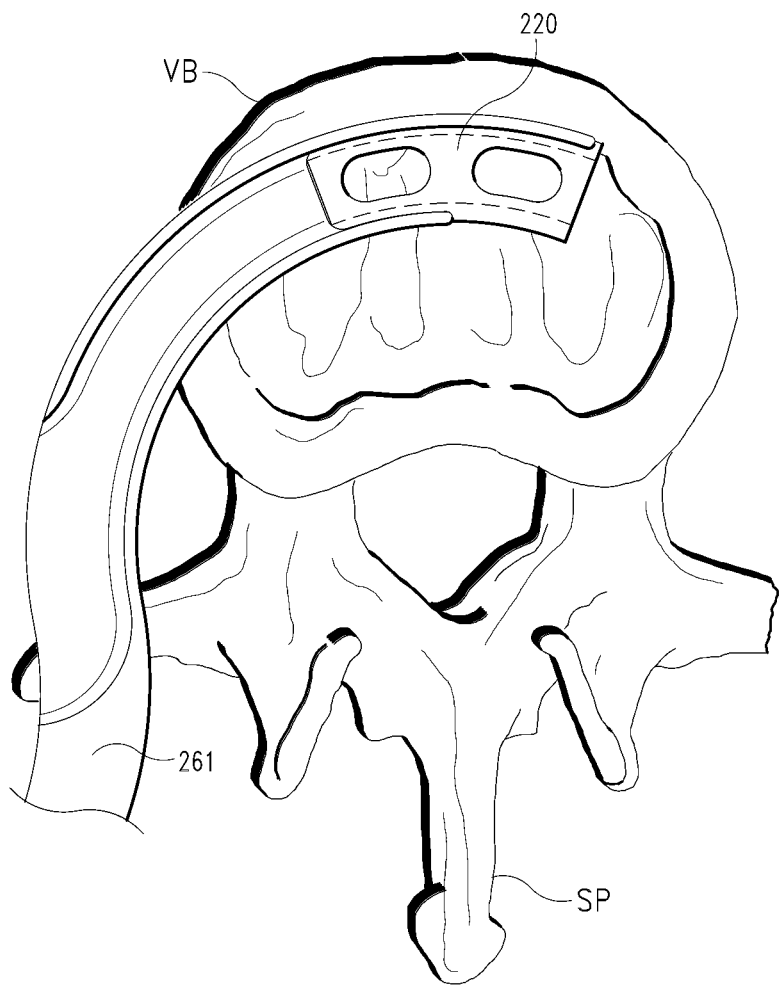
Figure 5E:
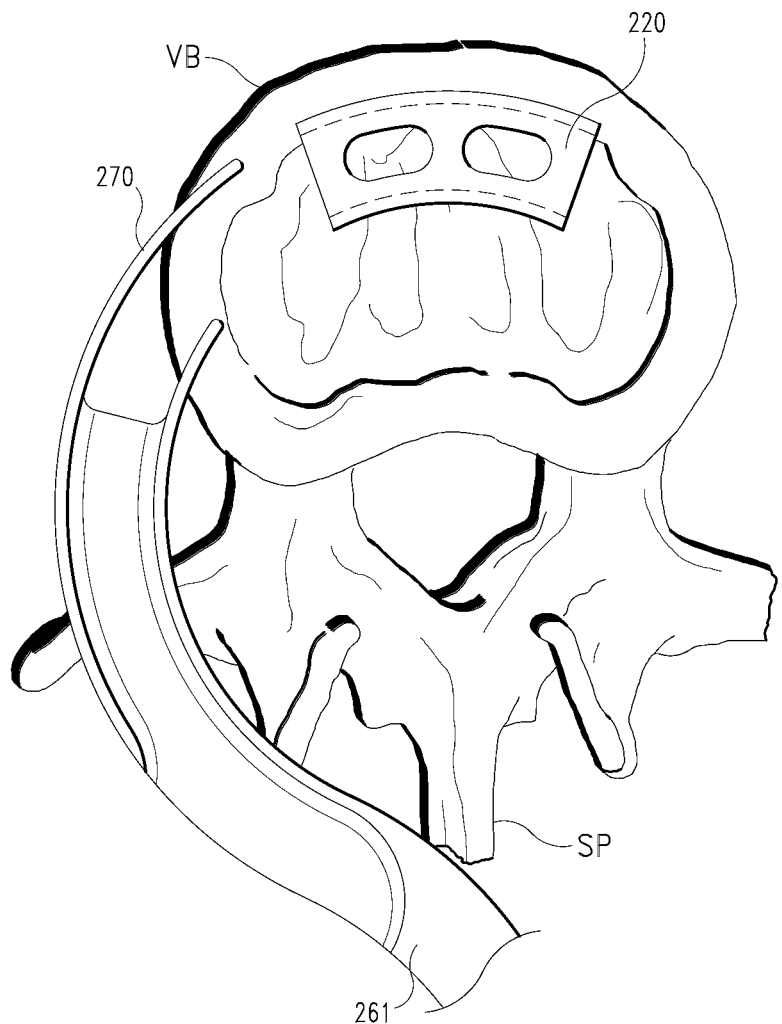
Figure 5F:
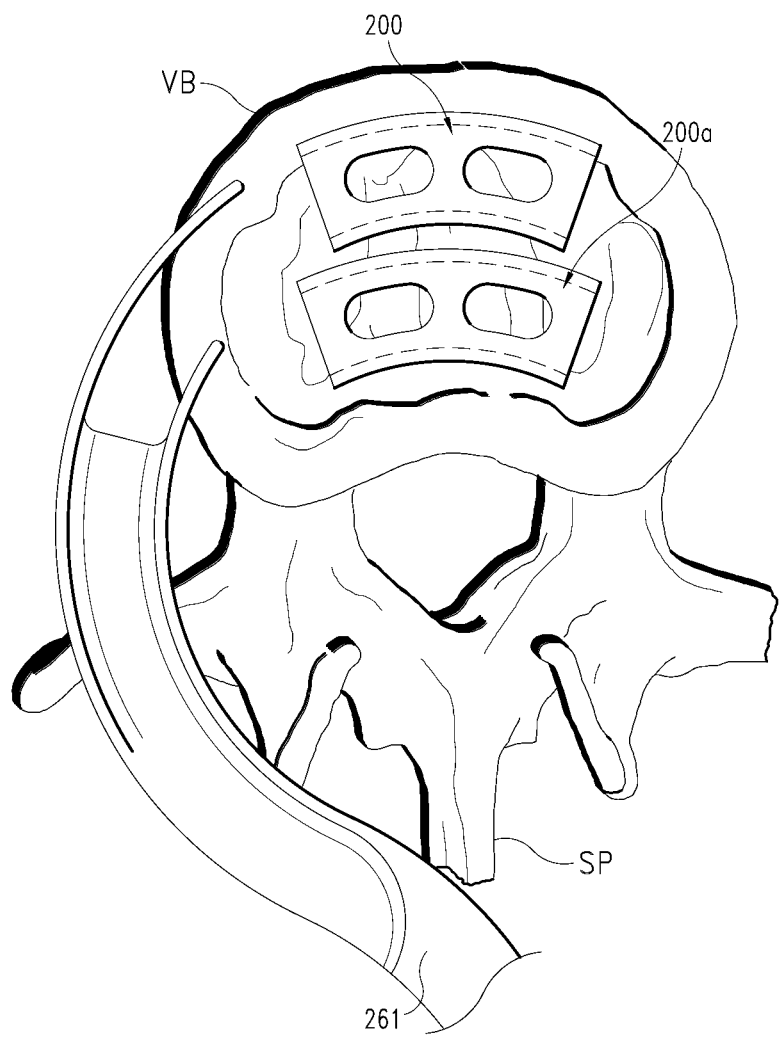

Surgery may be done implanting one, two (see FIGS. 5f (implant 200 and implant 200a), 11b (implant 400 and implant 400a)), or more implant assemblies.

The spinal system may optionally include one or more instruments, including one or more distraction instrument 260, 460, 560 and/or 660. The instrument having a proximal end such as 562 or 662 (see FIGS. 15a and 21a) and a distal end, 261, 461, 561, 661.

Figure 21A:
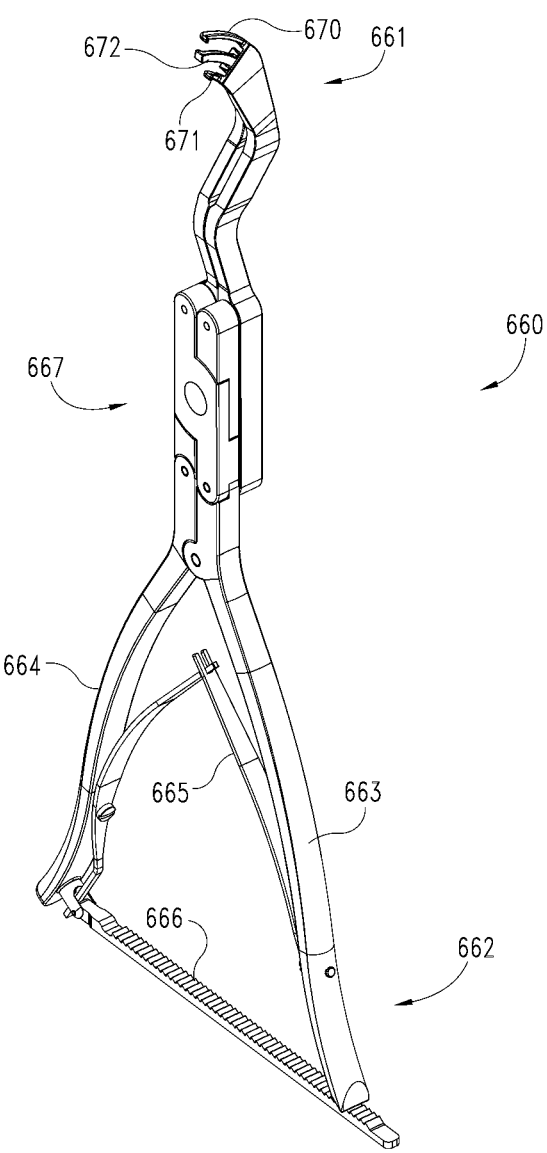
FIGS. 21a-21j are various views of another distractor instrument.
Figure 21B:
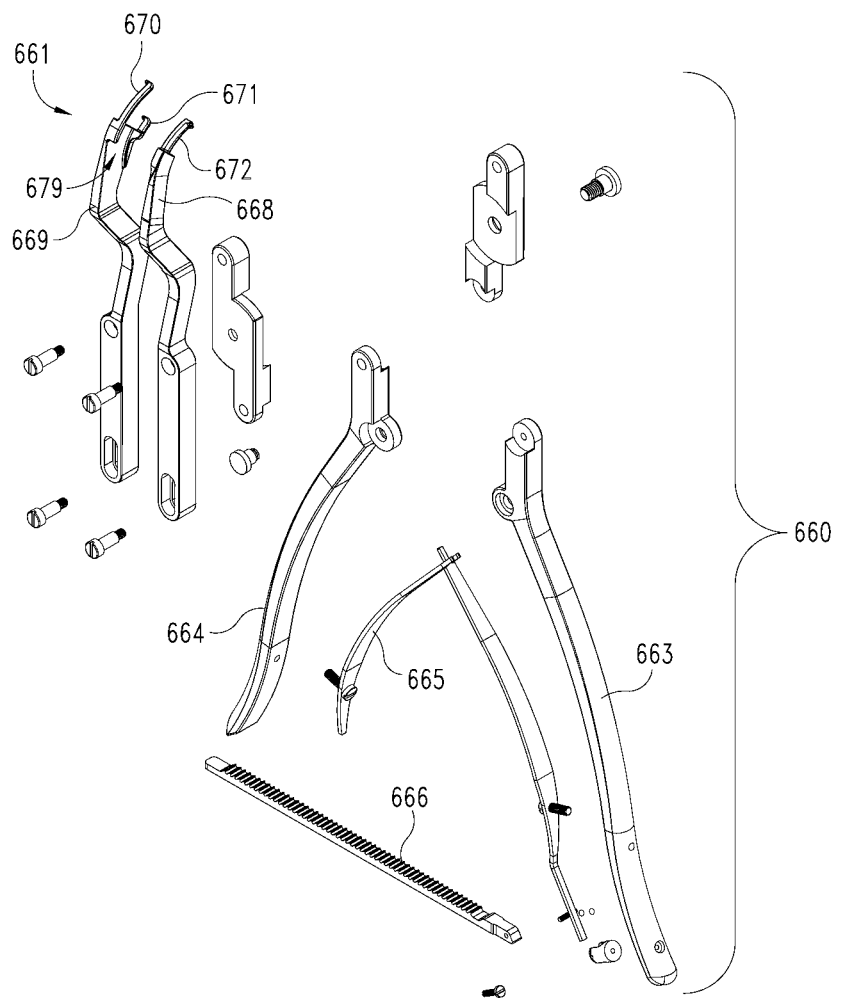
Figure 21C:
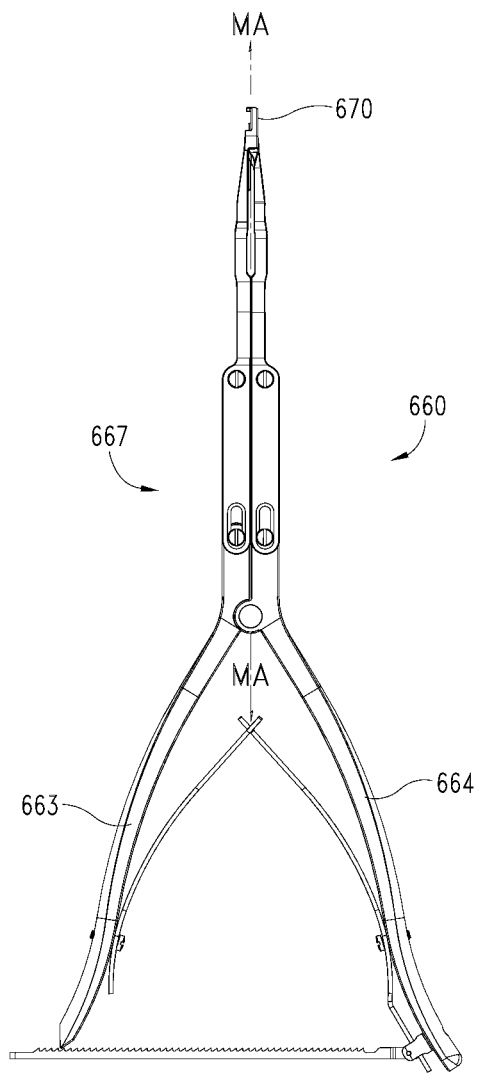

A distractor may be of any design. FIGS. 21a-21j show one example of distractor 660, and FIGS. 15a-15h show another similar one. They have, optionally and respectively, a first handle 663, 563, a second handle 664, 564, a spring 665, 565 which may urge the handles open (or closed), and optional position lock 666, 566, and a hinge system, such as for example a parallel, double pivot scissor mechanism 667, 567 for distal arms 668, 568 and distal arms 669, 569 to move apart or together, such as in parallel. FIG. 21b shows parts of an exemplary distractor 660 in an exploded view.

Optionally, the distal end has one or more mountings adapted to be loaded with the first footing and the second footing (see for example, FIGS. 6, 9, 10, 16a, 16b, 22a, 22b and 22c). These mountings may impart opposed distracting force at least in part through the first footing and the second footing to distract the first vertebral body and the second vertebral body. By way of example, one or more such mountings may comprises at least one or more curvilinear prong 270, 271 (FIGS. 5e and 60, prongs 570, 571 and 572 (FIGS. 15a-16b) and/or prongs 670, 671 and 672 (FIGS. 21a-23g) extending in at least one curvilinear path.

While optional, the prongs or other tracks or guides may have perpendicular projections to help engage the implant parts, such as the footings. For example, prongs 270 and 271 have projections 270a and 271a, respectively (see FIG. 6); prongs 570, 571 and 572 have projections 570a, 571a and 572a, respectively (see FIGS. 15h, 16c); and, prongs 670, 671 and 672 have projections 670a, 671a and 672a, respectively (see FIGS. 21e-21g). When used, such projections of the prong may fit into corresponding recesses or contact a surface. For example, projections 270a and 271a may contact a distal end (leading surface) of footing 220 (see FIG. 6). Other examples include projection on prong 572 engaging cross bar/surface 594a (see FIG. 13b), or projection 672a of prong 672 on the cross bar 694a (see FIG. 18d) surface of footing 620 (see FIGS. 22a, 22b, 23a). Other examples are the projection of prong 571 in recess 693a and/or the projection of prong 570 in recess 592a, and projection of prong 671a in recess 693a (see FIG. 22a) and/or the projection of prong 670a in recess 692a (see FIG. 22a).

One optional configuration with the first footing and/or the second footing collectively define or defines one, two, three, four, or more curvilinear tracks for receiving corresponding curvilinear prongs. For example, prongs 570 and 571 of a distraction instrument, may be received by curvilinear tracks 592 and 593 of footing 530. Central prong 572 may be received extending through a central region of a footing 520 (see FIGS. 13a, 13c and 13e). Optionally, axial recess 594 may be provided, in support 540 or in a footing, to leave a larger path for removal of prong 572. Other tracks and paths may include those as shown or described, including without limitation 670 into path 692, 671 into 693 (see FIGS. 17a, 22a), and straight versions of tracks or prongs 470 into 492, 471 into 493 (see FIGS. 10 and 12), and otherwise such as track 461 (see FIG. 11b).

Figure 21D:
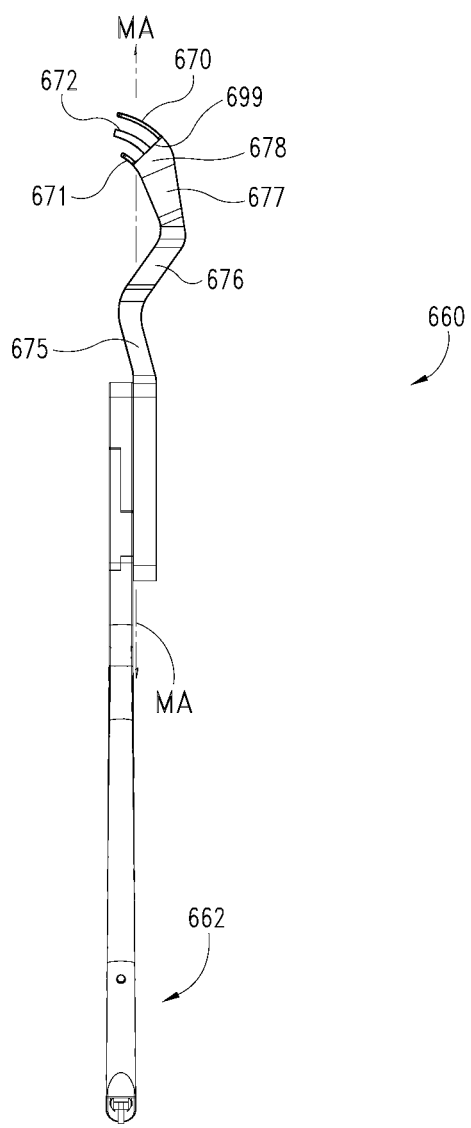
Figure 21E:
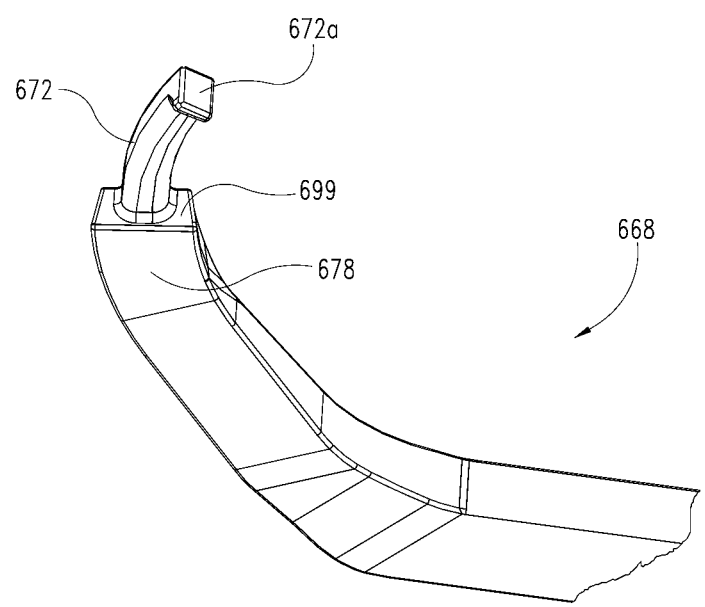
Figure 21F:
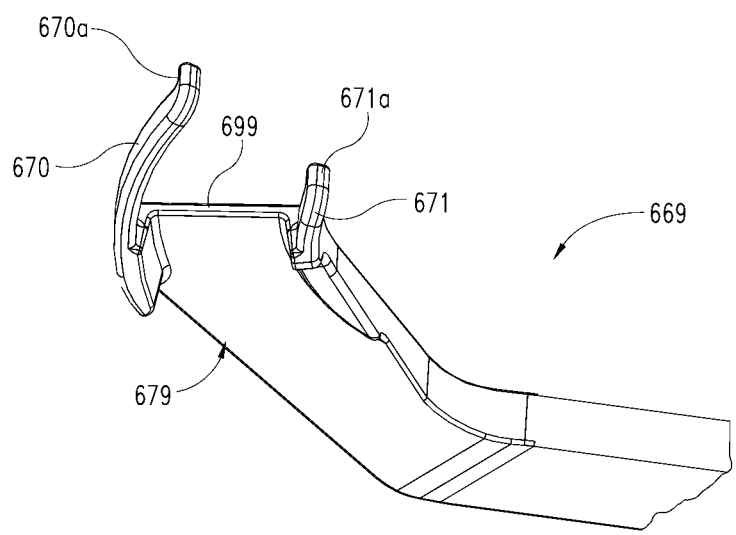
Figure 21G:
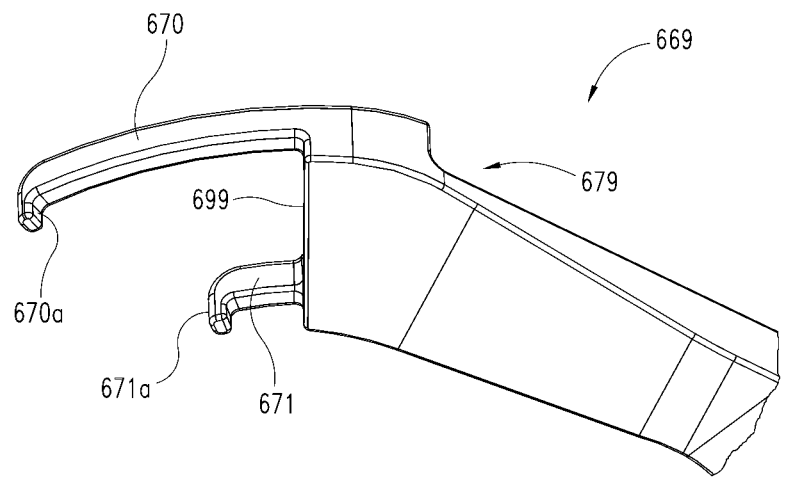

When the distracting instrument defines a curvilinear path, and the instrument may be adapted to be insertable with the support in the curvilinear path proximal of the distal end of the instrument. For example, support 140 is shown being insertable in a opening in distal end 261 in FIG. 6. Other examples are opening 279 (FIG. 5b), opening 470 (FIG. 11b), opening 579 (FIG. 15e), and/or opening 679 (FIGS. 21b, 21g). The support is advanceble along the path (curvilinear or otherwise) of the instrument into the path (curvilinear or otherwise) of the footings.

A distraction instrument having a proximal end 662, 562 and a distal end 661, 561 may have a major axis MA (see for example FIGS. 21c and 21d, or FIGS. 15b and 15d) oriented therealong, the instrument adapted to be loaded with the first footing and the second footing at the distal end. Optionally, the instrument, at its distal end, may provide for inter-vertebral insertion along a path which is generally perpendicular to the major axis. An example of this is showns in FIG. 21j with major axis MA and with path 672T forming generally perpendicular angle Y. Path 672T is tangent to the distal most portion of prong 272 in this example. This may be used in surgical methods approching the spine anteriorly, anterolaterally, and/or posteriorly. For example, in FIG. 23a-23g, a posterior, Transforaminal Lumbar Interbody Fusion (TLIF) approach is schematically diagrammed. The generally perpendicular feature facilitates avoiding or mininmizing contact with the nerve roots from the foramina. In such approach, for example, the implant and instruments may be inserted between nerve roots R1 and R2 (see e.g. FIGS. 23a-23g). Other approaches, such as trans-pedicular, see FIGS. 11a and 11b (normally with a straight, rather than curvilinear, instrument and implants), anterior, or otherwise may be used.

The surgeon may use the system as sequentially shown in, for example, FIGS. 23a-23g. They show a plan view (top or bottom, depending on whether footing 630 is on the top or bottom, respectfully). Optionally, prior distraction between vertebral bodies may be done (or not). The instrument 660, preferably loaded with the two footings, 620, 630, is introduced into the surgical site (see FIG. 23a). Its distal end is advanced between nerve roots R1 and R2 with the distal, leading edge placed between the vertebral bodies, typically at or near their edge (see FIG. 23b). The distractor may be distracted, at least partially, or not. The footings are advanced until they are between adjacent verbral bodies (see FIG. 23c). The footings also may be positioned and/or repositioned to a final location (see FIG. 23d) between the vertebral bodies. The distractor instrument and the footings are distracted (moving vertically) and creating a path for the insert. The insert 640 may be preloaded in the instrument, but optionally is side, back or top loaded into the intrument (see FIG. 23e), and then the insert 640 is advanced along the path between the footings. (see FIG. 23f). The instrument is withdrawn, leaving the implant assembly (see FIG. 23g) in position between the vertebral bodies. As before, this may optionally be repeated with more than one such set of footings and inserts. Optionally, inserts of progressively increasing height may be inserted then withdrawn to aid in distraction. Optionally, with two or more implant assemblies, that may be done alternating from one assembly and the other to progressively distract the vertebral bodies.

Figure 6:
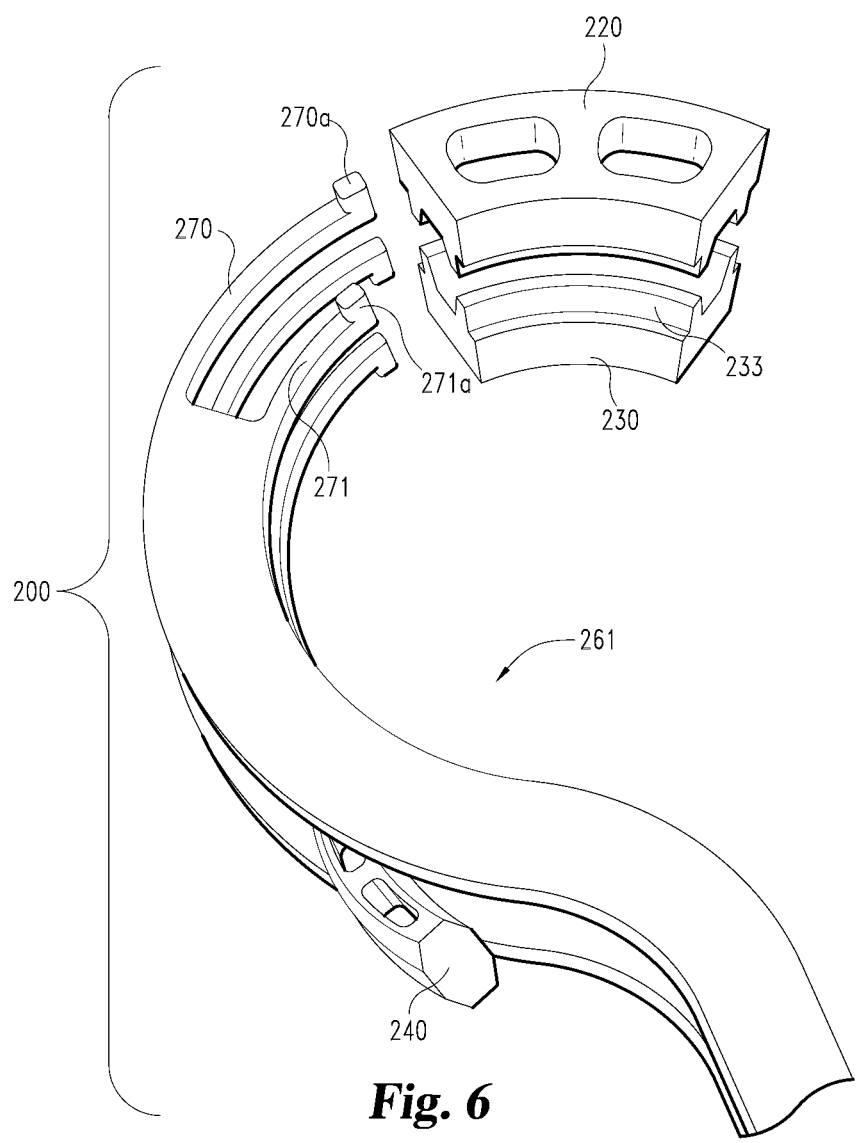
FIG. 6 is a perspective view of a distraction instrument and implant system.
Figure 15A:
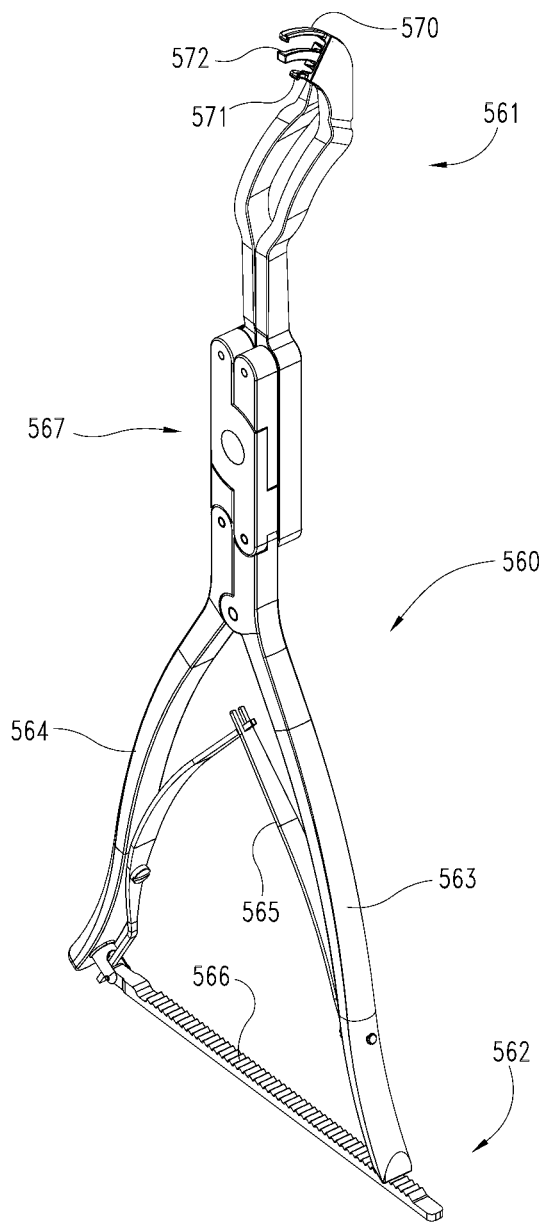
FIGS. 15a-15h are various views of a distractor instrument.
Figure 15B:
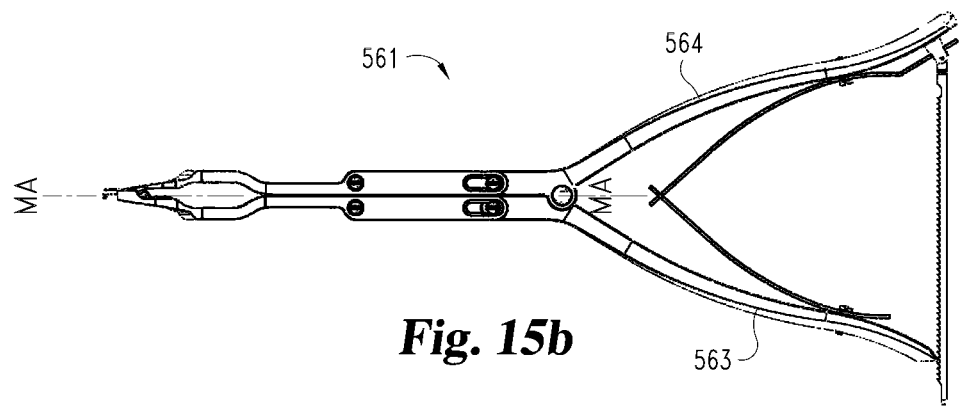
Figure 15C:
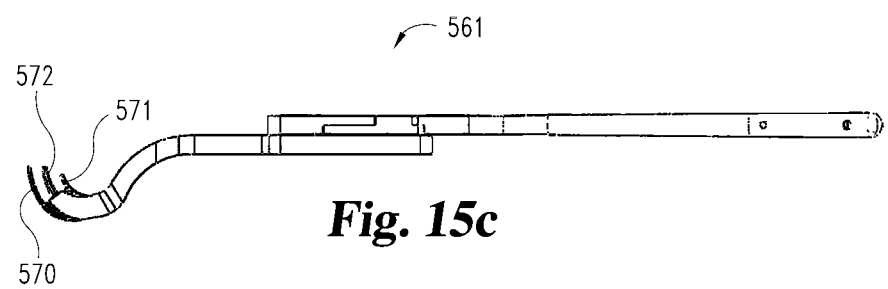
Figure 15D:
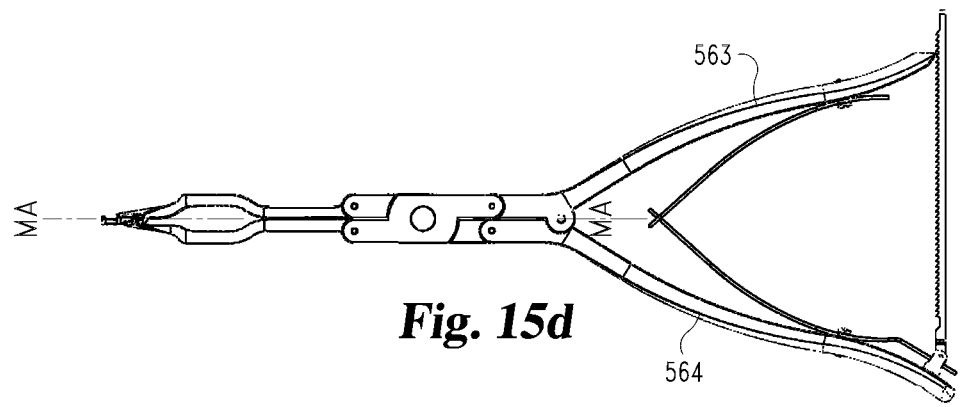
Figure 15E:
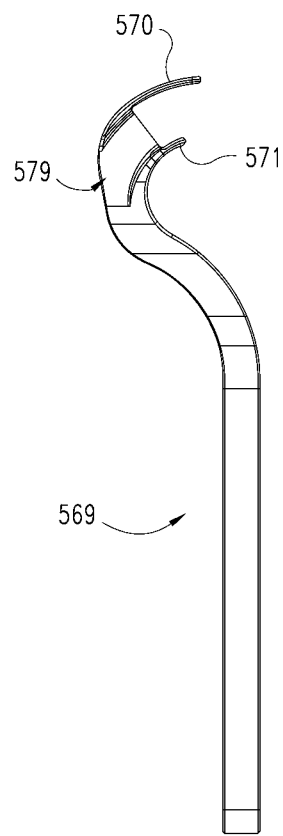
Figure 15F:
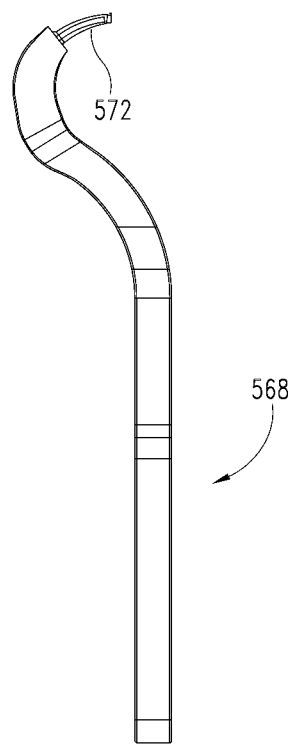
Figure 15G:
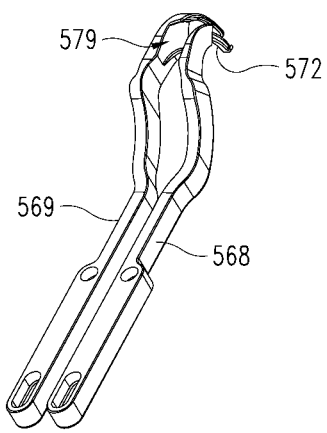
Figure 15H:
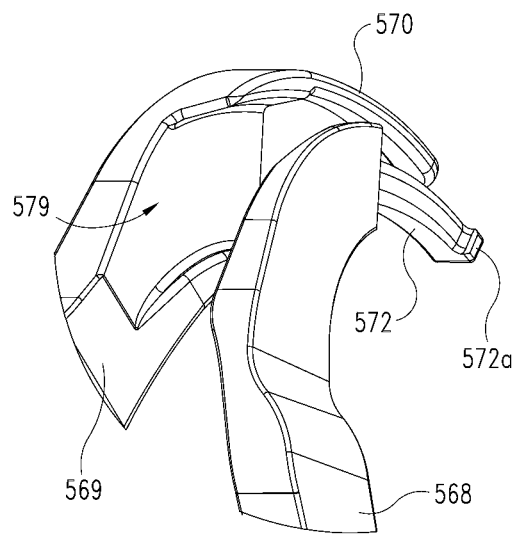
Figure 16A:
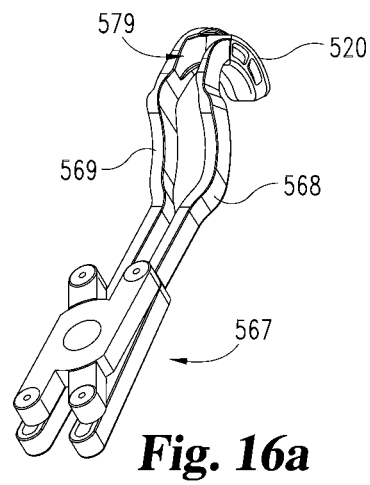
FIGS. 16a-16c are various views of the distractor instrument of FIGS. 15a-15h loaded with the implant of FIGS. 13a-14b.
Figure 16C:
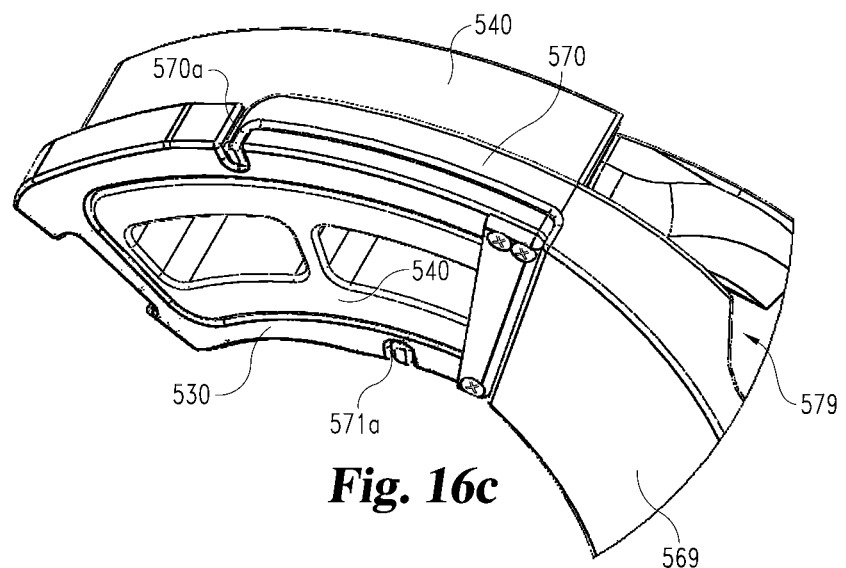
Figure 16B:
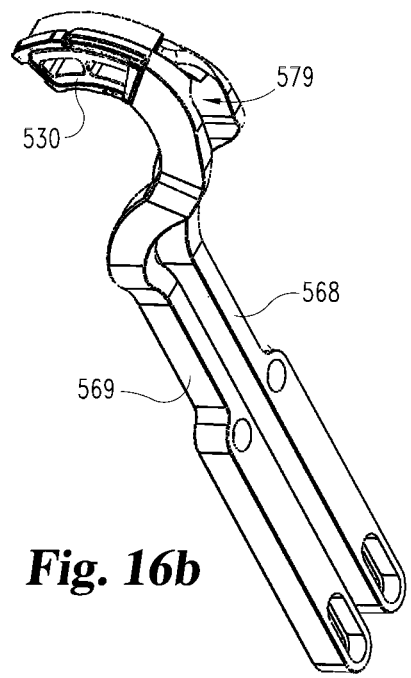

Optionally the distractor instrument, at its distal end, may have a zig-zag with respect to the major axis. For example, with respect to instrument 660, as seen at FIG. 21d, the distal end has segments, such as segment 676 that zigs and segment 677 that zags. This can facilitate surgical placement, such as avoiding nerve roots and/or other structure. FIG. 21d, illustrates a zig-zag-zig in segements 675, 676 and 677 (and segment 678). FIGS. 6 and 15c show a simple zig-zag.

Figure 21H:
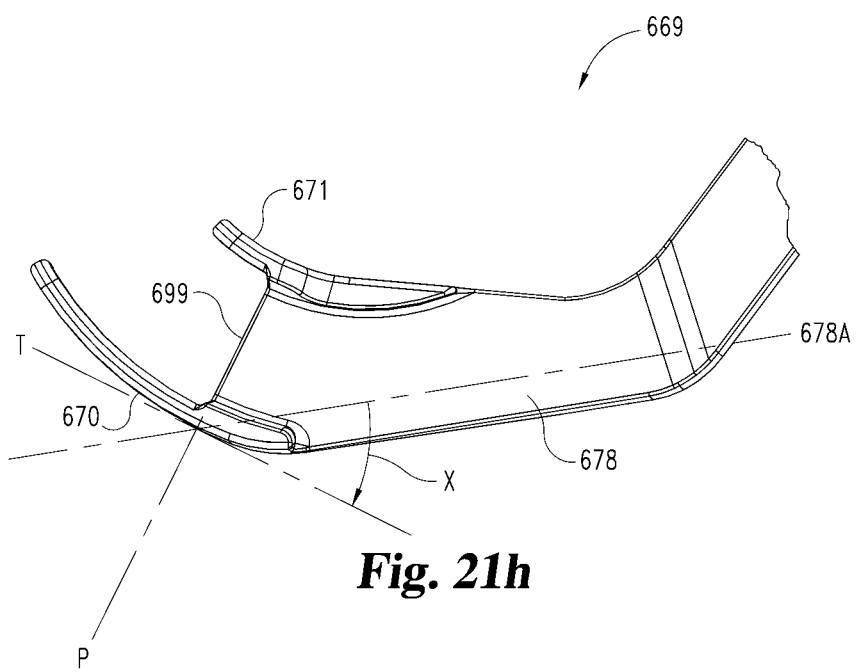
Figure 21I:
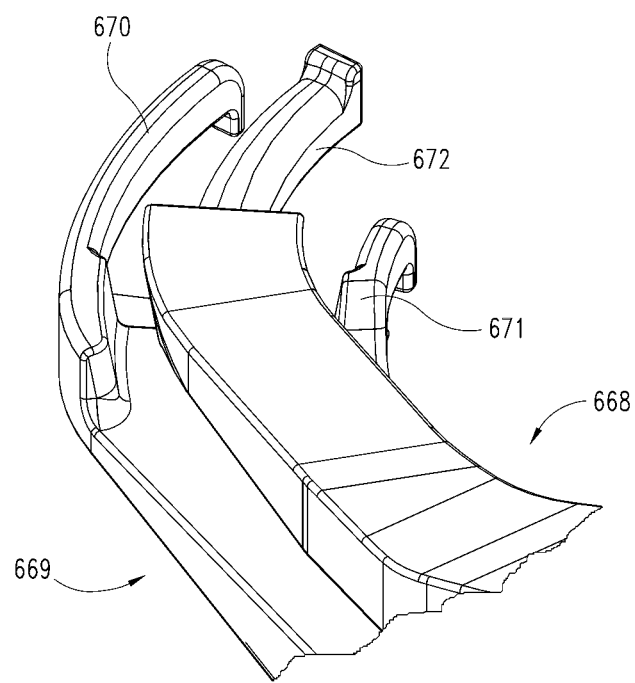
Figure 21J:
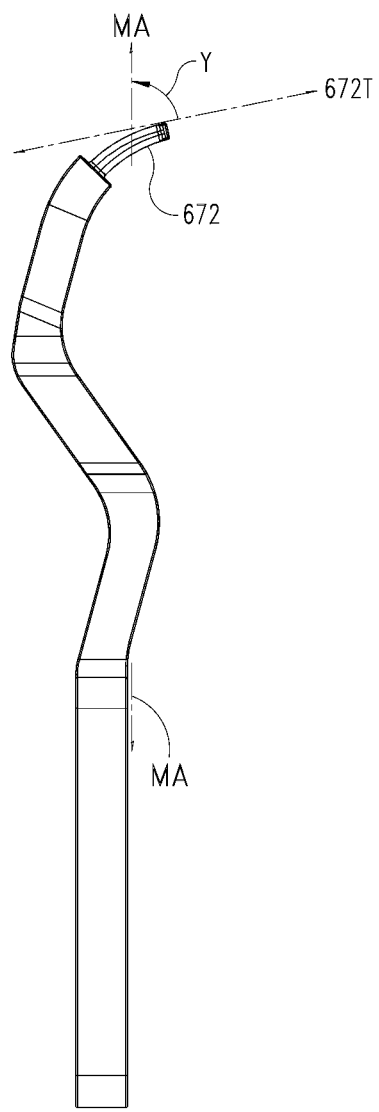
Figure 22A:
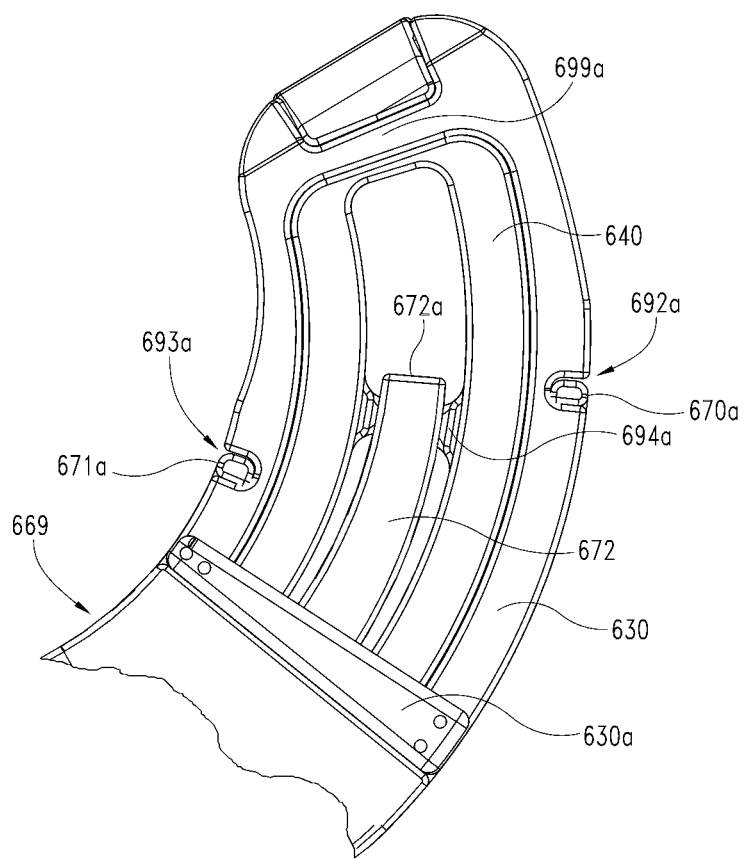
FIGS. 22a-22c are various views of the distractor instrument of FIGS. 21a-21j loaded with the implant of FIGS. 17a-20e.
Figure 22B:
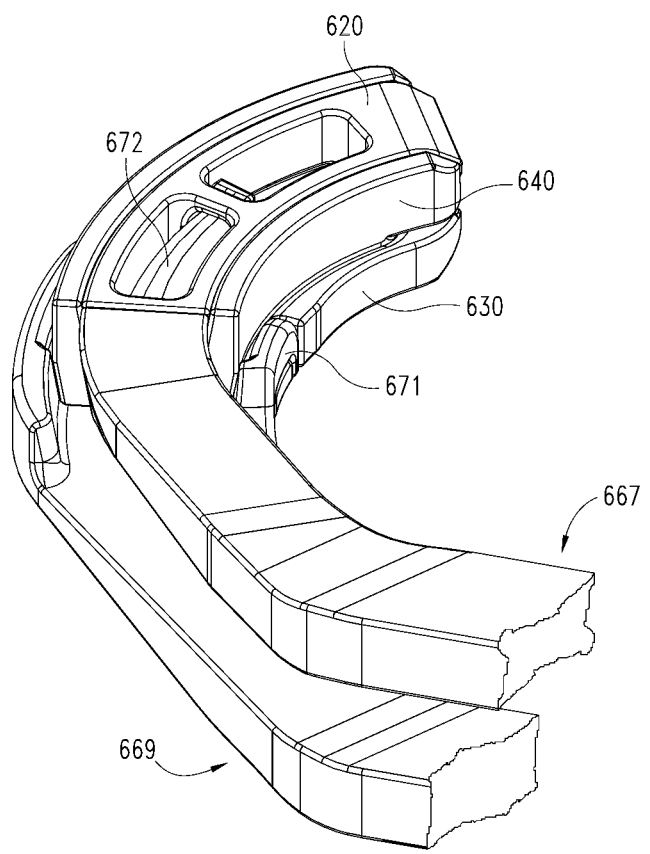
Figure 22C:
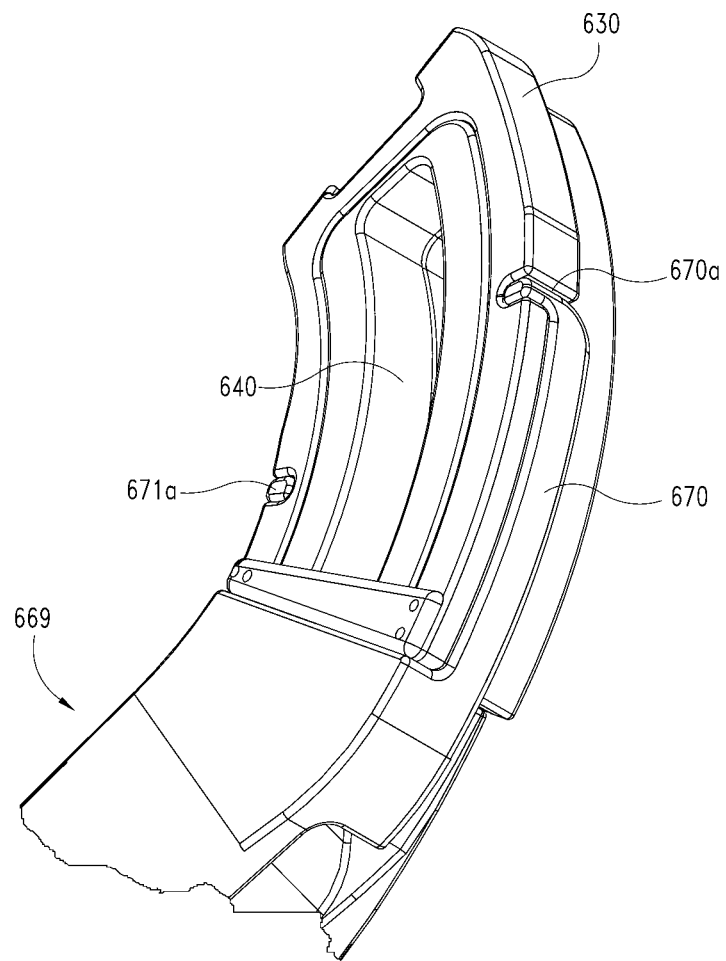
Figure 23:
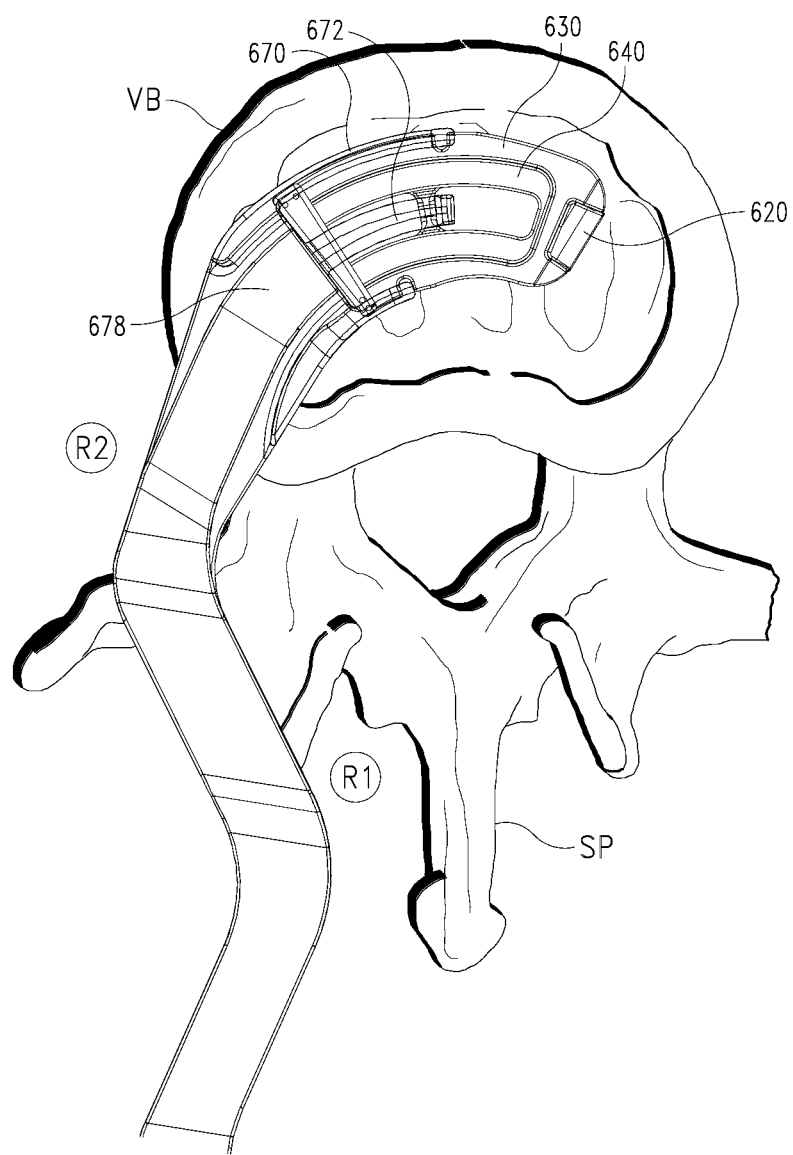
FIGS. 23a-23g are plan views, in sequence, of an example of the implantation of the system of FIGS. 22a-22c.
Figure 23A:
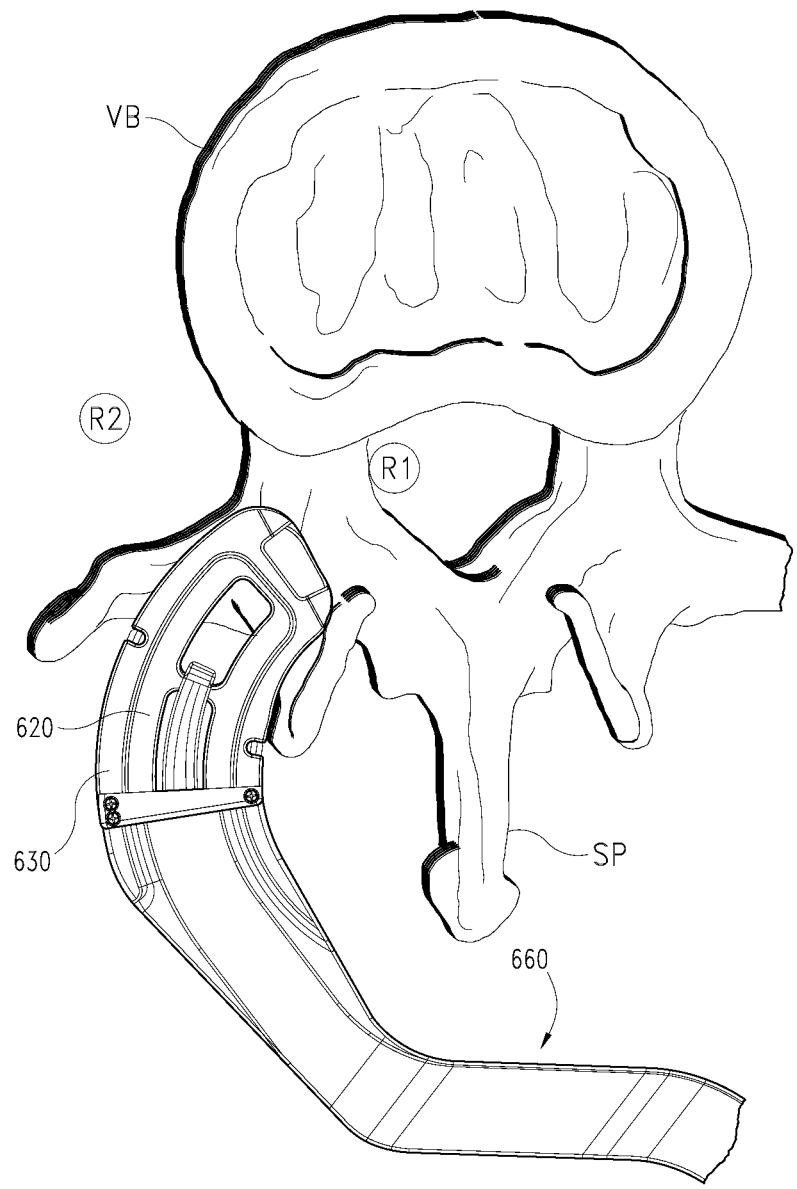
Figure 23B:
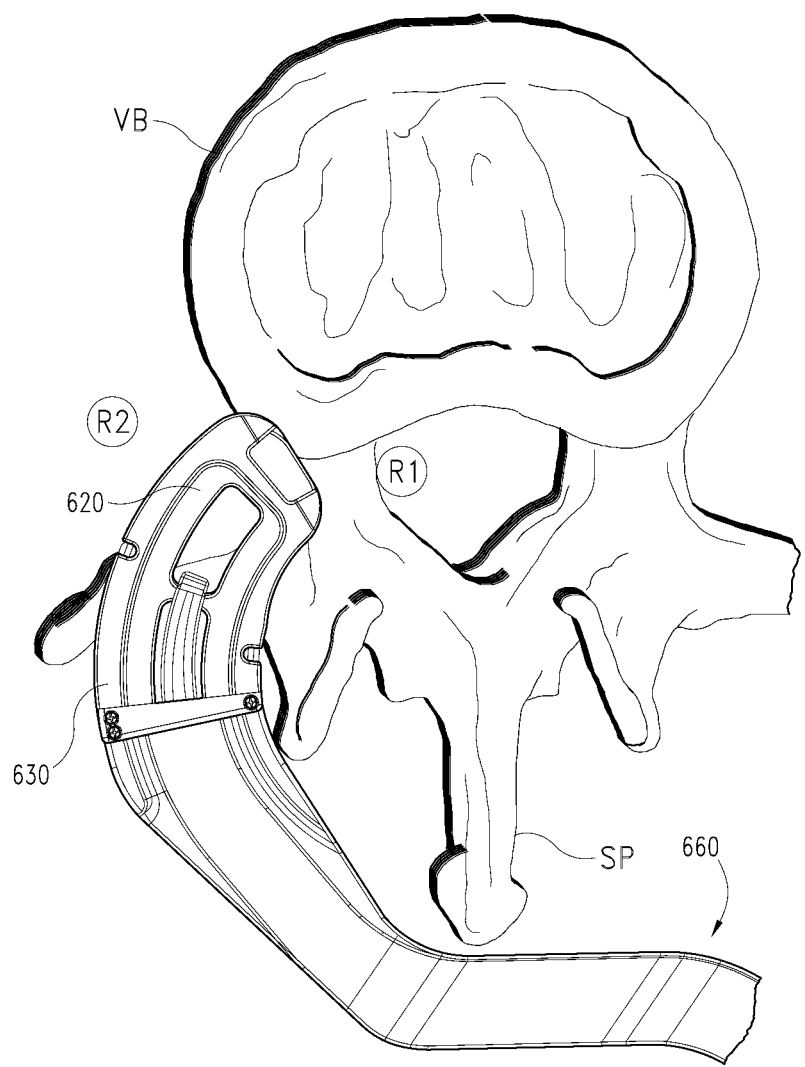
Figure 23C:
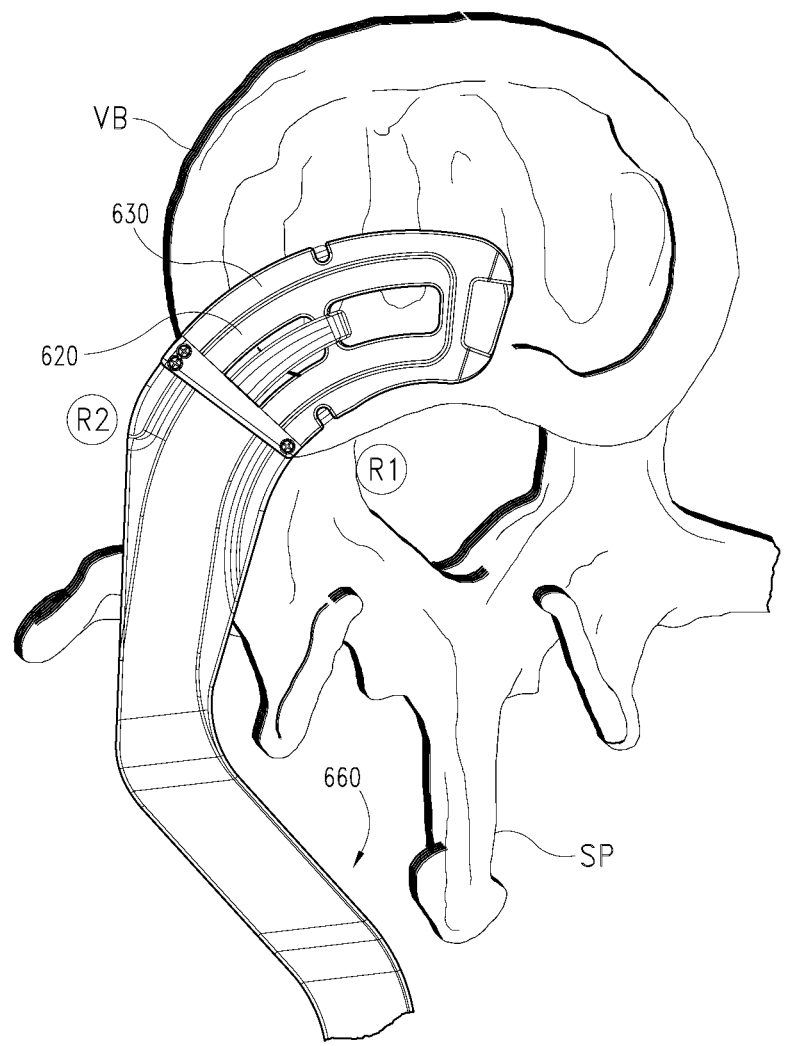
Figure 23D:
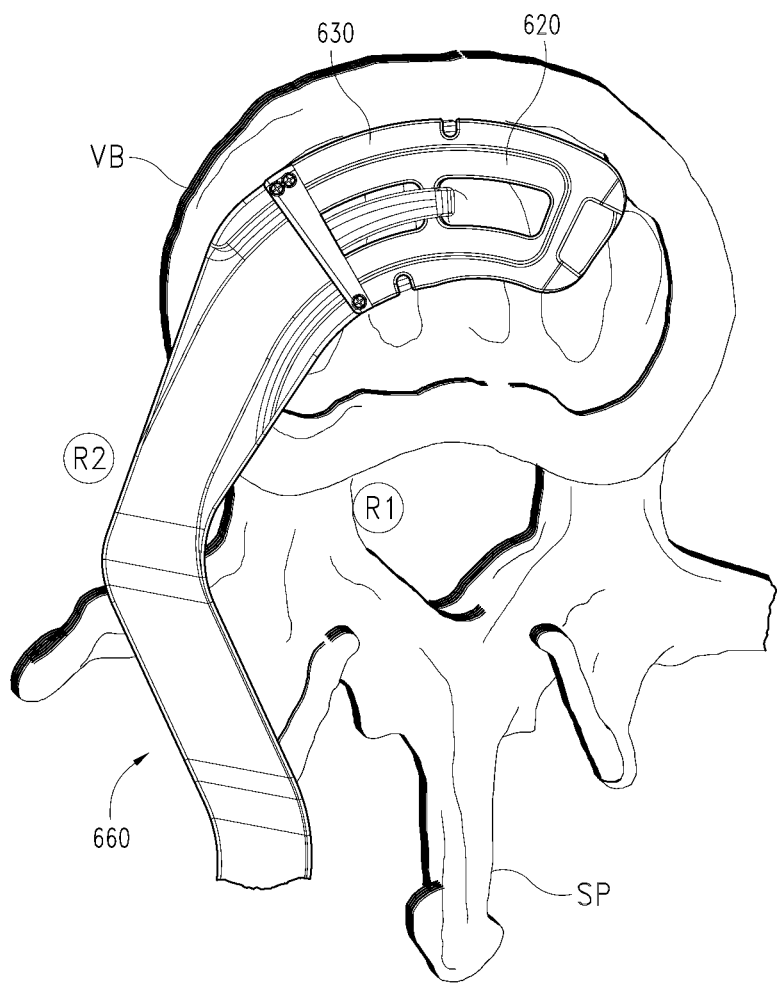
Figure 23E:
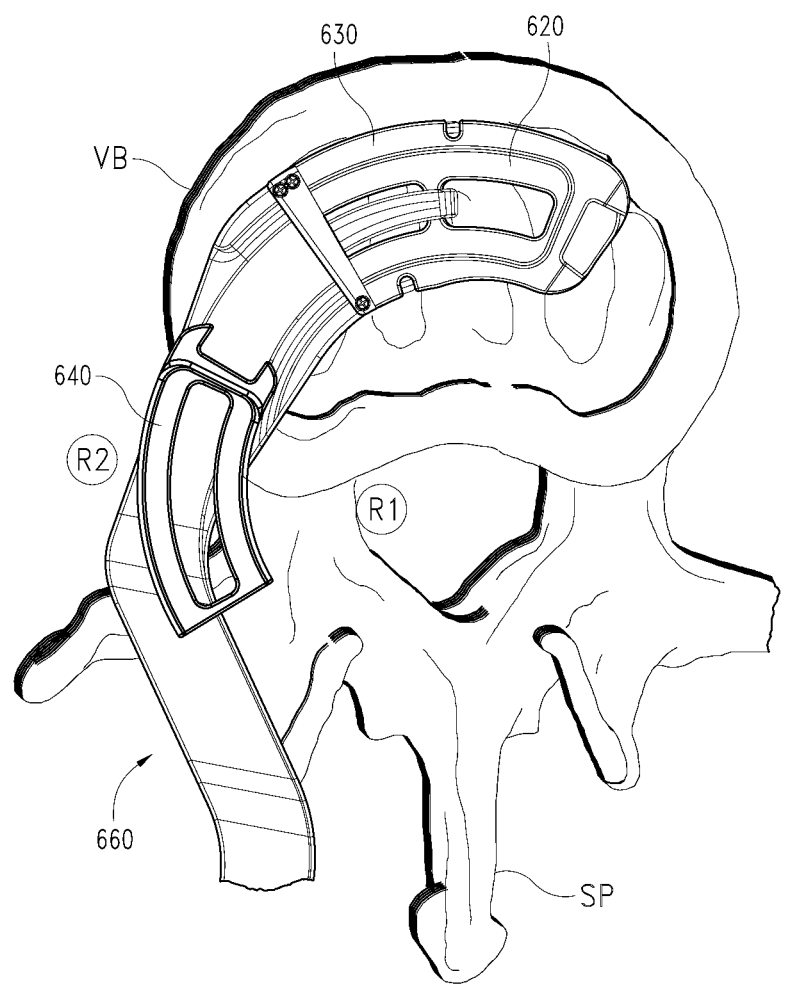
Figure 23F:
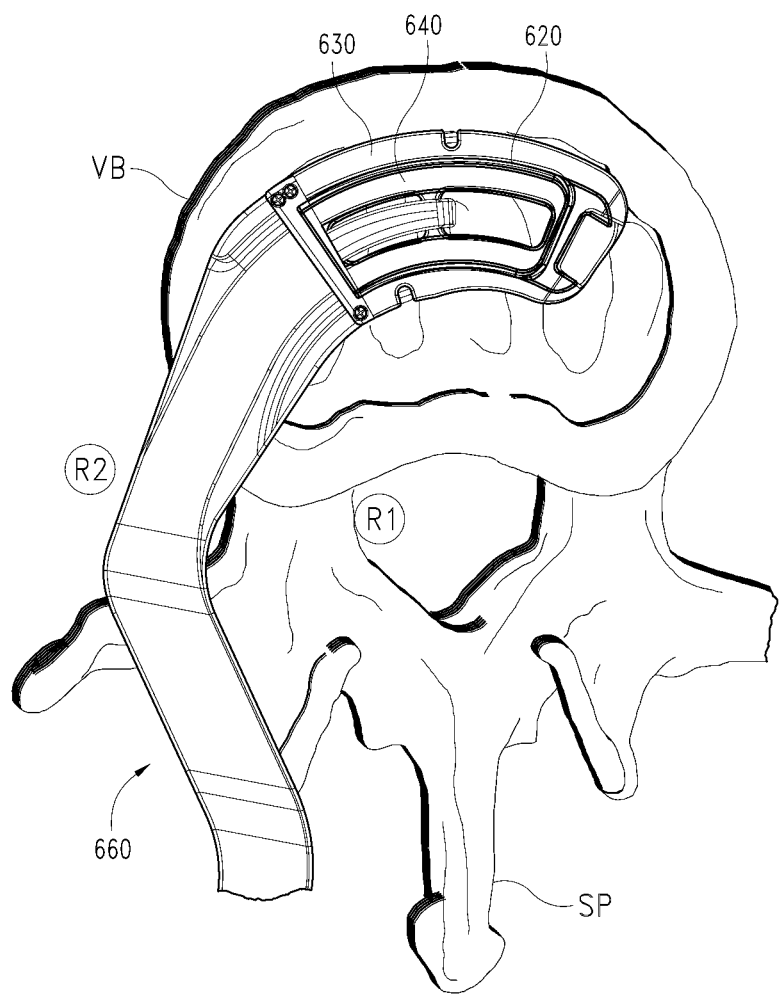
Figure 23G:
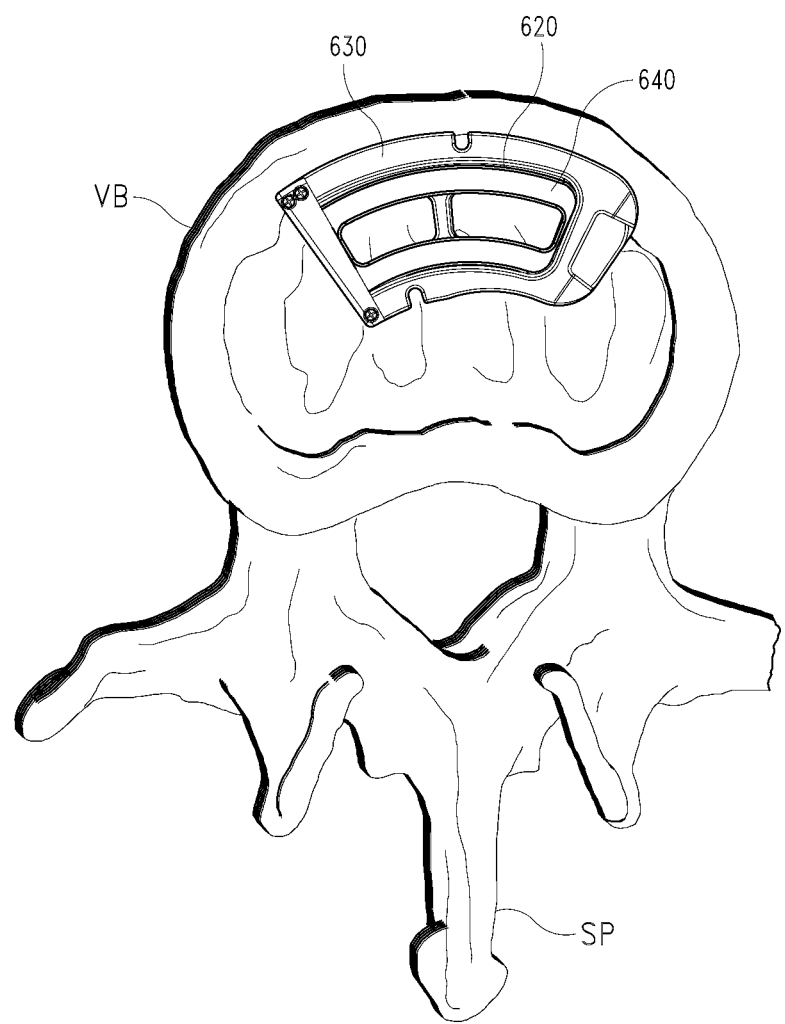

Another optional feature is having a separation edge at a particular angle with respect to the prongs when prongs are used. For example, as shown in FIG. 21h, an angle X is formed between the tangent line T (tangent to the intersection of separation edge 699, projected at line P) and axis 678A. Axis 678A is a longitudinal axis of the final, distal segment 678 (see also FIG. 21d) ending in edge 699 at the intersection of P and T. Angle X may be most any angle, but it optionally is believed to be optimal for TLIF procedures with angle X between about 30 degrees and 60 degrees, and more preferrably about 46 degrees. This too may facilitate positioning of the instrument (vis-a-vis nerve roots and otherwise) and inserting the support from the instrument into the footings, and also helps facilitate the removal of the prongs and/or instrument when the implant is left in positioned between the vertebral bodies, such as shown in FIG. 23g.

Figure 14A:
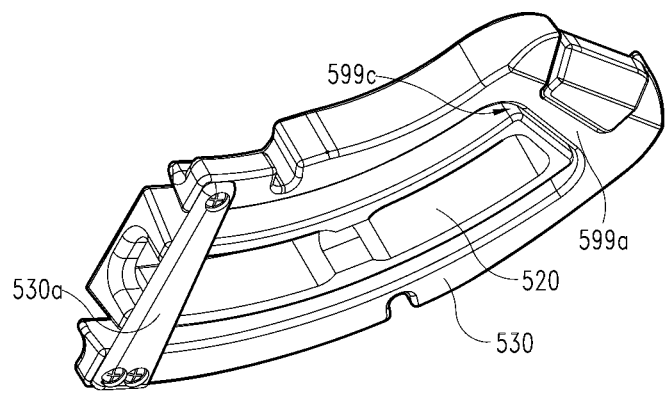
FIGS. 14a and 14b are perspective and rear elevation views of the implant of FIGS. 13a-13e without the support.
Figure 14B:
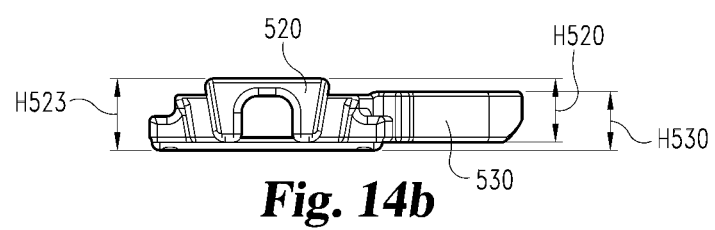
Figure 18A:
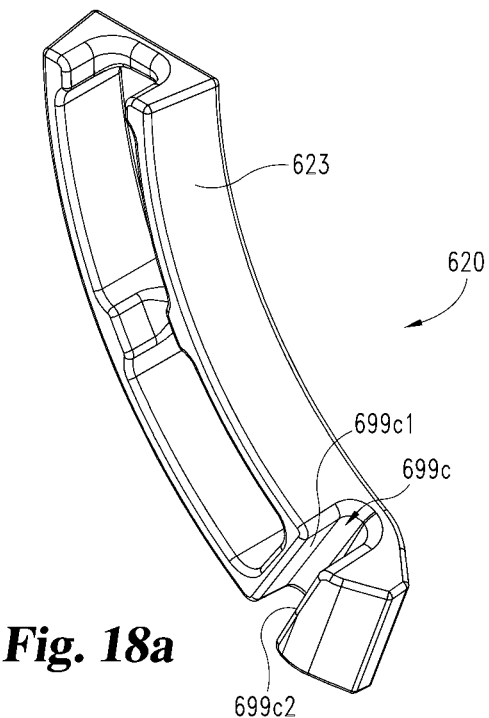
Figure 18B:
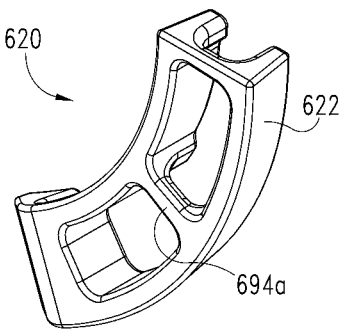
Figure 18E:
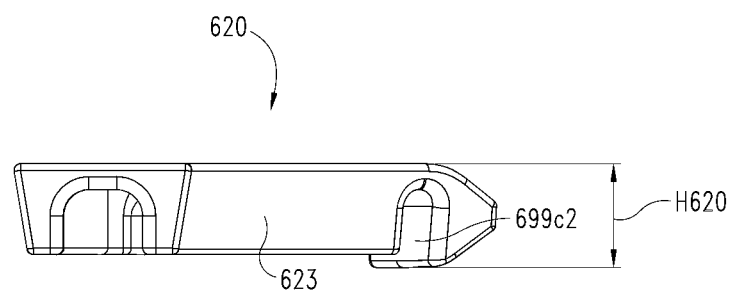
Figure 19A:
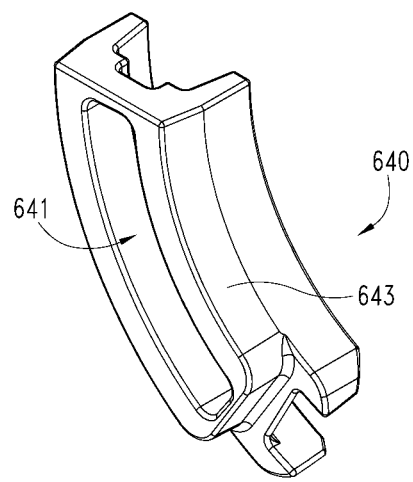
FIGS. 19a-19e are views of an implant support of FIG. 17a shown in isolation, with 19a and 19b being perspective views, 19c a side elevation, 19d a plan view, and 19e a rear elevation.
Figure 19B:
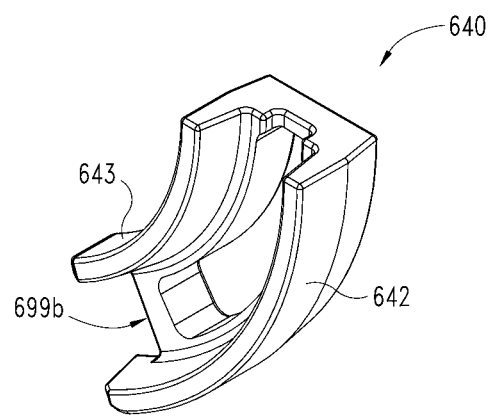
Figure 19C:
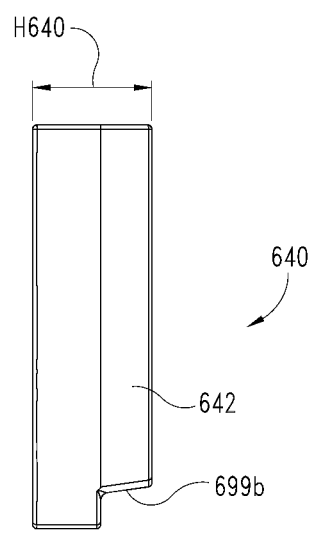
Figure 19D:
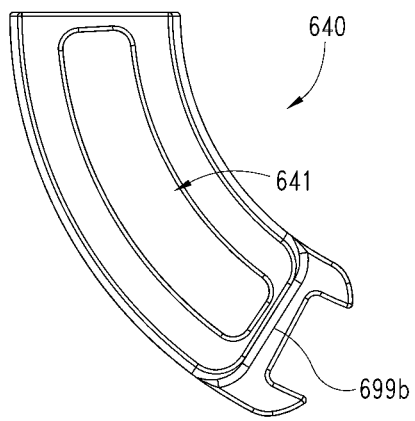
Figure 19E:
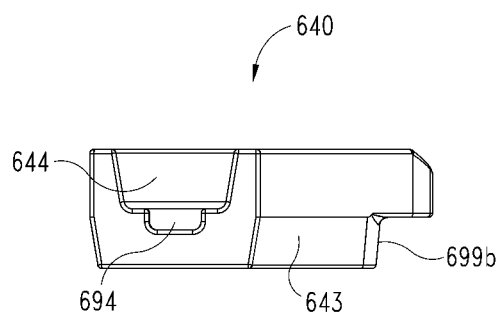
Figure 20A:
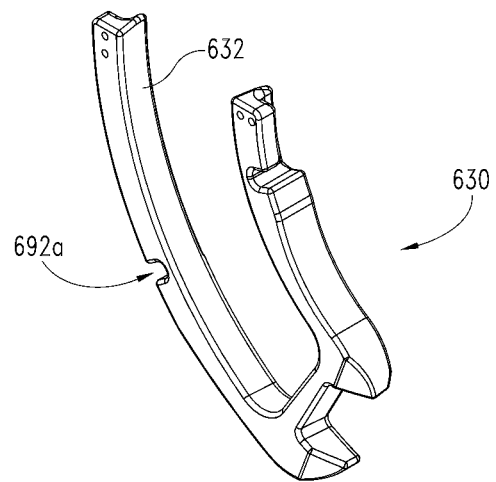
FIGS. 20a-20e are views of an implant footing of FIG. 17a shown in isolation, with 20a and 20b being perspective views, 20c a side elevation, 20d a plan view, and 20e a rear elevation.
Figure 20B:
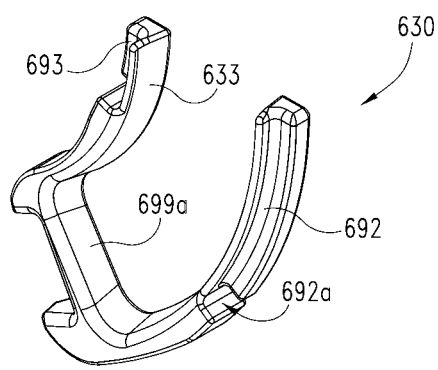
Figure 20C:
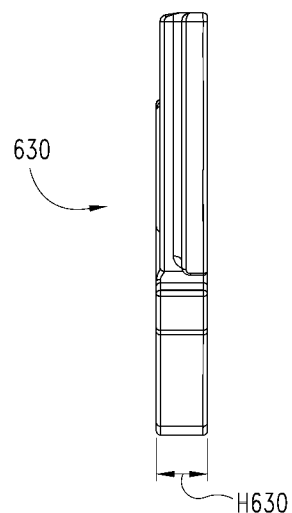
Figure 20D:
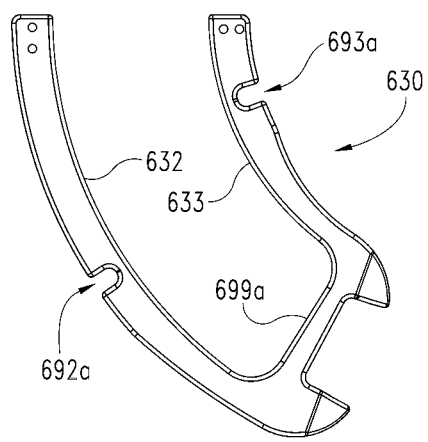
Figure 20E:
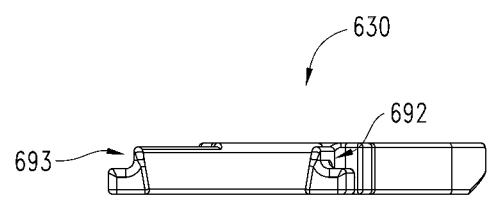

The footings may, optionally, be adapted to be nested with respect to each other, and/or with respect to the support. For example, the first footing and the second footing are, prior to insertion between the first and second vertebral bodies, adapted to be nested with one another to form a footing assembly such that the height of the nested footing assembly is less than the sum of: (a) a height of the first footing, and (b) a height of the second footing. An example is seen in FIGS. 14a and 14b. Footing 520 and footing 530 are nested with respect to each other. The height H523 of the nested footing assembly (FIG. 14b) is less than the sum of: (a) the height H530 of footing 530 and height H520 of footing 520. This height relationship is likewise present when footing 620 and 630 are nested together (without a support therebetween). See for example, height H630 (FIG. 20c), height H640 of the support (FIG. 19c), and height H620 of footing 620 (FIG. 18e). Regarding implant 200 shown at FIG. 4b, since the rails of the two footings are aligned, such configuration would not normally result in nested footings. However, this (and the other designs, FIG. 4a, 10) may optionally be modified to provide nesting of the footings. For example in FIG. 4b, rails 222 and 223 may be moved wider or narrower or staggered with respect to rails 233 and 232.

The height H523 of the nested footing assembly 520, 530 or 620, 620 is optionally one or both: (a) less than 6 millimeters; and (b) not more than approximately the height of one the footings with the greatest height, either H520 or H530. Even more preferably, the height of the nested footing assembly (see for example FIG. 14b) is less than or equal to about 4 millimeters. This helps facilitate interting the footing assembly between two verterbral bodies.

Note that, for example, FIGS. 14a and 14b show a footing assembly (without a support, and prior to insertion of a support) as compared to FIGS. 13b-13e which illustrate the footings separated and with a support 540 therebetween, forming a footing-support-footing assembly. Other such footing-support-footing assembly examples are show in FIGS. 2, 9, 10 and 17b-17e.

The footings and supports may slide with respect to each other. For example with respect to implant 500 (see FIG. 13a), the first footing 520 and the support 540 may have at least a first pair of slide-interfaces at surface 523 and opening 544 defined by sufaces on 540. The second footing 530 and the support 540 may have at least a second pair of slide-interfaces at surfaces 532, 533 and surfaces on support 540 such as surfaces 543, 542. Optionally, such first pair of slide interfaces and the second pair of slide interfaces are offset from each other as illustrated. Also, optionally, the support may nest in one or both footings, as support 540 nests in footing 530, and/or the one or both footings may nest in the support, as footing 520 nests in support 540. And, optionally, a footing-support-footing assembly may have, at least one slide interface of the first pair of slide interfaces nested within the second pair of slide interfaces. Preferably, but optionally, the support and the first and second footings are adapted to collectively form a footing-support-footing assembly having an assembly height H500 (see FIG. 13c) that is less than the sum of: (a) a height of the support H540, and (b) a height H520 or H530 (see FIG. 14b) of one of the footings. This is present in implants assemblies 100, 200, 400 and 600, and also of assemblies 300 and 500 measured at a common relative point along their central axis. Some or all of these attributes of implant 500 described in this paragraph are likewise present in implant 600, and its components, of FIGS. 17a-20e, as height H620 and H630 (respective footings), height H640 (support) and height H600 (assembly). Likewise, tracks 123, 122, 133 and 132 (FIG. 4a) provide a groove, such as 124, for support 140 to slide. Likewise, tracks 223, 222, 233 and 232 (FIG. 4b) provide a groove, such as 224, for support 240 to slide. Track 433 (FIG. 12) is another example.

Preferably, when the support slides with respect to a footing, it is along a direction parallel to their central axis, such as central axis CA1, CA2, CA3, CA4, CA5 or CA6 as shown in the illustrated examples.

The implant assembly, and its subcomponent footing(s) and/or support, each ordinarily have a front or leading side, and an opposite rear or trailing side. The leading side is the left side of FIGS. 17a and 17b, and is the right side of FIGS. 13a and 13b. Other examples are symetric.

Figure 13B:
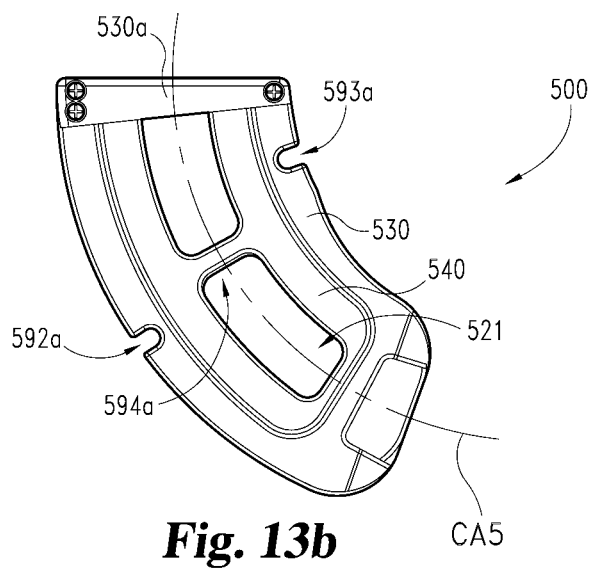
Figure 13C:
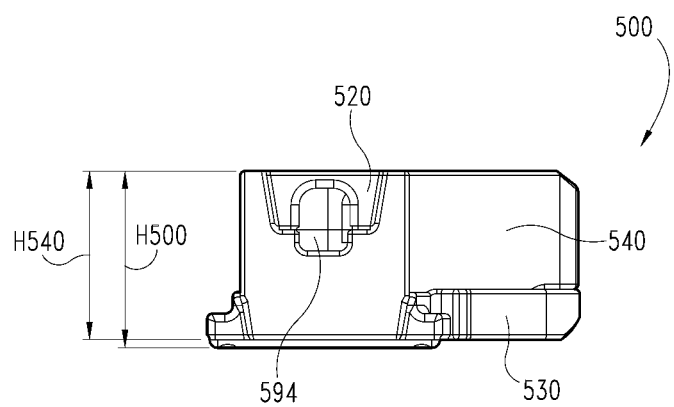
Figure 13D:
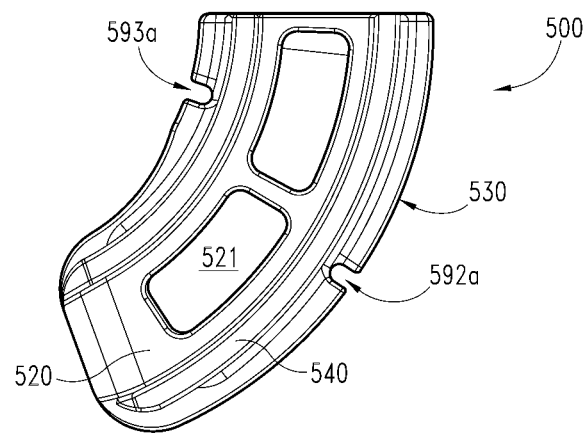
Figure 13E:
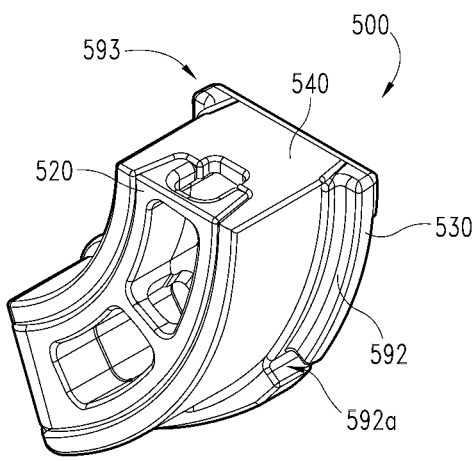

The spinal system may form a solid implant or mostly solid implant. However, preferably but optionally, it may also be such that the first footing, the second footing and the support form a cage having one or more void, preferably a central void adapted to be filled with bone growth material and openings exposing the void to the first and second vertebral bodies. Examples of such central voids include 141 (FIGS. 1, 2 and 4a), 241 (FIG. 4b), 341 (FIGS. 7-9), 441 (FIG. 10), and 541 (FIGS. 13a, 13b and 13d). The openings, such as 121, 221, 321, 521, 621 are illustrated in the corresponding footings, providing a conduit or opening from the void to the vertrabral body bone.

Optionally, the implant assembly is flat on the top and bottom, such as with implant assemblies 200, 400, 500 and 600. However, optionally, they may be non-parallel such as shown at angle 125 with respect to bone engaging surface 126 (see FIGS. 2 and 4a) to accommodate spinal curavture in the direction of the width of the implant, and/or with longitidunal tapering (see FIG. 9) at angel 327 with respect to bone engaging surface 328. Optionally, such angulation may be acheived by having the support (instead or in addition to the footing(s)) having angulation, laterally and/or longitudinally. The bone engaging surfaces of the footings, angled or not, may be smooth, rough, grooved, porous, or otherwise.

While the support is normally slideable with respect to one or both footings, optionally but preferrably a stop to stop advancement of the support along the path may be provided. Such is shown, for example with respect to implant 500 in which cross bar surface 599a (see FIG. 13a) provides a stop for support 540 at front facing surface 599b. Note further, that if the footings are nested (without support 540) such as when loaded on the distractor, recess forming surface 599c engages surface 599a, causing interlocking and acting as a stop. Implant 600 has similar surfaces 699a, 699b and 699c (see FIG. 17a) performing this stopping function. Surfaces 699c1 may provide contact in pushing in a distal direction and surface 699c2 (FIG. 18a) may provide contact in pulling in a proximal directions.

Preferably, the footings are loaded onto the distractor before distraction. See e.g. FIGS. 16c, 16d, 22a-22c. With the vertical distraction force imparted via the distractor and the loaded footings, the support or supports are thereafter inserted. Optionally, however, the distractor may distract the two vertebral bodies, and thereafter (or during) the footings advanced (see FIGS. 5a-5f), and thereafter the support(s) advanced within the footings. Such advancement, footings and/or supports, may be done anyway, typically a pusher using compression force (see for example force arrows C and D in FIG. 9), manually, by mallet or otherwise.

The footings (top and bottom) and the support may be provided in a kit, such as a serilizable package (e.g. autoclavable tray or otherwise). The kit may include multiple sizes, including an array of various footing width, length, curvature, and/or angulation, and correponding supports. The supports may include various heights and/or other previously mentioned geometries. Temporary supports may be provided (plastic or otherwise) to help distraction by incremental insertion followed by removal followed by insertion of a higher support. Instrument kits may be provided apart and/or with the implants.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by following claims are desired to be protected. All publications, patents, and patent applications cited in this specification are herein incorporated by reference as if each individual publication, patent, or patent application were specifically and individually indicated to be incorporated by reference and set forth in its entirety herein.

What is claimed is:

1. A spinal implant system, comprising:
   a first footing adapted for inter-vertebral contact with a first vertebral body;
   a second footing adapted for inter-vertebral contact with a second vertebral body adjacent to the first vertebral body; and
   a support slideably insertable between said first footing and said second footing;
   wherein said footings provide a curvilinear path; and
   wherein said support is adapted to be insertable by being advanced in a curvilinear path along said curvilinear path of said footings while said first and second footings are in-situ between said first and second vertebral bodies,
   wherein said first footing, said second footing and said support are interlocked to form a rigid body;
   wherein said first footing and said second footing are longer along said curvilinear path than their respective width;
   wherein said first footing and said second footing each have a transverse footprint which is smaller than 500 square millimeters;
   and further comprising a distraction instrument, said instrument having a proximal end and a distal end; and, said distal end having a plurality of mountings adapted to be loaded with said first footing and said second footing.

2. The spinal system of claim 1 wherein said mountings impart opposed distracting force at least in part through said first footing and said second footing to distract said first vertebral body and said second vertebral body.

3. The spinal system of claim 1 wherein on at least one of said footings said mounting comprises at least one curvilinear prong extending in at least one curvilinear path.

4. The spinal system of claim 3 wherein said distracting instrument defines a curvilinear path, and said instrument is adapted to be insertable with said support in said curvilinear path proximal of said distal end of said instrument, and wherein said support is advanceble along said curvilinear path of said instrument into said curvilinear path of said footings.

5. A spinal implant system, comprising:
   a first footing adapted for inter-vertebral contact with a first vertebral body;
   a second footing adapted for inter-vertebral contact with a second vertebral body adjacent to the first vertebral body; and,
   a support slideably insertable between said first footing and said second footing;
   wherein said footings provide a curvilinear path; and
   wherein said support is adapted to be insertable by being advanced in a curvilinear path along said curvilinear path of said footings while said first and second footings are in-situ between said first and second vertebral bodies;
   wherein said first footing and said second footing collectively define at least three curvilinear tracks for receiving corresponding curvilinear prongs of a distraction instrument, at least one of said curvilinear tracks extending through a central region of a footing.

6. A spinal implant system, comprising:
   a first footing adapted for inter-vertebral contact with a first vertebral body;
   a second footing adapted for inter-vertebral contact with a second vertebral body adjacent to the first vertebral body; and,
   a support slideably insertable between said first footing and said second footing;
   wherein said footings provide a curvilinear path; and
   wherein said support is adapted to be insertable by being advanced in a curvilinear path along said curvilinear path of said footings while said first and second footings are in-situ between said first and second vertebral bodies;
   and further comprising a distraction instrument, said instrument having a proximal end and a distal end and a major axis oriented therealong, said instrument adapted to be loaded with said first footing and said second footing at said distal end; and,
   wherein said instrument, at its distal end, provides for inter-vertebral insertion along a path which is generally perpendicular to said major axis.

7. A spinal implant system, comprising:
   a first footing adapted for inter-vertebral contact with a first vertebral body;
   a second footing adapted for inter-vertebral contact with a second vertebral body adjacent to the first vertebral body; and
   a support slideably insertable between said first footing and said second footing;

wherein said footings provide a curvilinear path; and
wherein said support is adapted to be insertable by being advanced in a curvilinear path along said curvilinear path of said footings while said first and second footings are in-situ between said first and second vertebral bodies;
wherein said first footing and said second footing are, prior to insertion between said first and second vertebral bodies, adapted to be nested with one another to form a footing assembly such that a height of said nested footing assembly is less than the sum of: (a) a height of said first footing, and (b) a height of said second footing.

8. The spinal system of claim 7 wherein a height of said nested footing assembly is both: (a) less than 6 millimeters; and (b) not more than approximately the height of one said footings with the greatest height.

9. A spinal implant system, comprising:
a first footing adapted for inter-vertebral contact with a first vertebral body
a second footing adapted for inter-vertebral contact with a second vertebral body adjacent to the first vertebral body; and
a support slideably insertable between said first footing and said second footing;
wherein said footings provide a curvilinear path; and
wherein said support is adapted to be insertable by being advanced in a curvilinear path along said curvilinear path of said footings while said first and second footings are in-situ between said first and second vertebral bodies;
wherein said first footing, said second footing and said support are interlocked to form a rigid body;
wherein said first footing, said second footing and said support form a cage having a central void adapted to be filled with bone growth material and openings exposing said void to said first and second vertebral bodies.

10. The spinal system of claim 6 wherein at least one of said first and second footings comprise a stop to stop advancement of said support along said curvilinear path.

11. The spinal system of claim 1 wherein wherein said instrument, at its distal end, zig-zags with respect to said major axis.

12. A spinal implant system, comprising:
a first footing adapted for inter-vertebral contact with a first vertebral body;
a second footing adapted for inter-vertebral contact with a second vertebral body adjacent to the first vertebral body;
a support adapted to be slideably insertable between said first footing and said second footing;
said first footing, said second footing, and said support being adapted to be inserted with a distraction instrument having a proximal end and a distal end and a major axis oriented therealong, said instrument adapted to be loaded with said first footing and said second footing at said distal end; and,
wherein said instrument, at its distal end, provides for inter-vertebral insertion along a path which is generally perpendicular to said major axis; and,
wherein said first footing and said second footing are prior to insertion between said first and second vertebral bodies, adapted to be nested with one another to form a footing assembly such that the height of said nested footing assembly is less than the sum of (a) a height of said first footing, and (b) a height of said second footing.

13. The spinal system of claim 12 wherein wherein said instrument, at its distal end, zig-zags with respect to said major axis.

14. The spinal system of claim 12 wherein said first footing, said second footing and said support form a cage having a central void adapted to be filled with bone growth material and openings exposing said void to said first and second vertebral bodies.

15. A spinal implant system, comprising:
a first footing adapted for inter-vertebral contact with a first vertebral body;
a second footing adapted for inter-vertebral contact with a second vertebral body adjacent to the first vertebral body;
wherein said first footing and said second footing are, prior to insertion between said first and second vertebrae bodies, adapted to be nested with one another to form a footing assembly such that a height of said nested footing assembly is less than the sum of: (a) a height of said first footing, and (b) a height of said second footing; and,
a support adapted to be insertable between said first footing and said second footing.

16. The spinal system of claim 15 wherein said height of said nested footing assembly is less than 6 millimeters.

17. The spinal system of claim 16 wherein said height of said nested footing assembly is less than or equal to about 4 millimeters.

18. The spinal system of claim 15 wherein said height of said nested footing assembly is not more than approximately the height of one said footings with the greatest height.

19. The spinal system of claim 15 wherein said first footing, said second footing, and said support being adapted to be inserted with a distraction instrument having a proximal end and a distal end and a major axis oriented therealong, said instrument adapted to be loaded with said first footing and said second footing at said distal end; and,
wherein said instrument, at its distal end, provides for inter-vertebral insertion along a path which is generally perpendicular to said major axis.

20. A spinal implant system, comprising:
a first footing adapted for inter-vertebral contact with a first vertebral body;
a second footing adapted for inter-vertebral contact with a second vertebral body adjacent to the first vertebral body;
a support adapted to be slideably insertable between said first footing and said second footing;
wherein said first footing and said support have at least a first pair of slide-interfaces;
wherein said second footing and said support have at least a second pair of slide-interfaces; and,
wherein said first pair of slide interfaces and said second pair of slide interfaces are offset from each other.

21. The spinal system of claim 20 wherein said first and second footings and said support are adapted to collectively form a footing-support-footing assembly, wherein at least one slide interface of said first pair of slide interfaces is nested within said second pair of slide interfaces.

22. The spinal system of claim 20 wherein said support and said first and second footings are adapted to collectively form a footing-support-footing assembly having an assembly height that is less than the sum of (a) a height of said support, and (b) a height of one of said footings.

23. A spinal implant system, comprising:
a first footing adapted for inter-vertebral contact with a first vertebral body;

a second footing adapted for inter-vertebral contact with a second vertebral body adjacent to the first vertebral body; and a support slideably insertable between said first footing and said second footing;

wherein said footings provide a curvilinear path; and wherein said support is adapted to be insertable by being advanced in a curvilinear path along said curvilinear path of said footings while said first and second footings are in-situ between said first and second vertebral bodies;

wherein said support and said first and second footings are adapted to collectively form a footing-support-footing assembly having an assembly height that is less than the sum of: (a) a height of said support, and (b) a height of one of said footings.

* * * * *

UNITED STATES PATENT AND TRADEMARK OFFICE
CERTIFICATE OF CORRECTION

| | | |
|---|---|---|
| PATENT NO. | : 9,084,683 B2 | Page 1 of 1 |
| APPLICATION NO. | : 13/345154 | |
| DATED | : July 21, 2015 | |
| INVENTOR(S) | : Paul Nottingham | |

It is certified that error appears in the above-identified patent and that said Letters Patent is hereby corrected as shown below:

Claims
In Claim 1, col. 11, line 54, replace "path; and" with --path; and,--
In Claim 1, col. 11, line 59, replace "ies," with --ies;--
In Claim 5, col. 12, line 27, replace "path; and" with --path; and,--
In Claim 6, col. 12, line 46, replace "path; and" with --path; and,--
In Claim 7, col. 12, line 65, replace "body; and" with --body; and,--
In Claim 7, col. 13, line 1, replace "path; and" with --path; and,--
In Claim 9, col. 13, line 20, replace "body" with --body;--
In Claim 9, col. 13, line 23, replace "body; and" with --body; and,--
In Claim 9, col. 13, line 26, replace "path; and" with --path; and,--
In Claim 12, col. 13, line 62, replace "are prior" with --are, prior--
In Claim 12, col. 13, line 66, replace "of (a)" with --of: (a)--
In Claim 15, col. 14, line 17, replace "vertebrae" with --vertebral--
In Claim 22, col. 14, line 63, replace "of (a)" with --of: (a)--
In Claim 23, col. 15, line 3, replace "body; and" with --body; and,--
In Claim 23, col. 15, line 6, replace "path; and" with --path; and,--

Signed and Sealed this
Twenty-fourth Day of November, 2015

Michelle K. Lee
*Director of the United States Patent and Trademark Office*